(12) United States Patent
Cooks et al.

(10) Patent No.: US 8,932,875 B2
(45) Date of Patent: Jan. 13, 2015

(54) SYSTEMS AND METHODS FOR SAMPLE ANALYSIS

(75) Inventors: Robert Graham Cooks, West Lafayette, IN (US); Guangtao Li, Carmel, IN (US); Xin Li, West Lafayette, IN (US); Zheng Ouyang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 4 days.

(21) Appl. No.: 13/977,758

(22) PCT Filed: Dec. 29, 2011

(86) PCT No.: PCT/US2011/067771
§ 371 (c)(1),
(2), (4) Date: Sep. 4, 2013

(87) PCT Pub. No.: WO2012/094227
PCT Pub. Date: Jul. 12, 2012

(65) Prior Publication Data
US 2013/0344610 A1    Dec. 26, 2013

Related U.S. Application Data

(60) Provisional application No. 61/430,021, filed on Jan. 5, 2011.

(51) Int. Cl.
G01N 33/28  (2006.01)
H01J 49/26  (2006.01)
H01J 49/42  (2006.01)
H01J 49/04  (2006.01)

(52) U.S. Cl.
CPC ............. *H01J 49/42* (2013.01); *H01J 49/0431* (2013.01); *H01J 49/0459* (2013.01)

USPC ............ 436/173; 436/60; 436/141; 436/181; 422/83; 250/282; 250/283; 250/285; 250/424; 250/425

(58) Field of Classification Search
USPC ............ 436/60, 141, 147, 173, 181; 250/281, 250/282, 283, 284, 285, 288, 289, 424, 250/425; 422/83
See application file for complete search history.

(56) References Cited

U.S. PATENT DOCUMENTS

| | | | |
|---|---|---|---|
| 4,885,076 A | 12/1989 | Smith et al. | |
| 5,152,177 A | 10/1992 | Buck et al. | |
| 6,297,499 B1 | 10/2001 | Fenn | |
| 6,982,416 B2 | 1/2006 | Villinger et al. | |
| 7,154,088 B1 | 12/2006 | Blain et al. | |

(Continued)

FOREIGN PATENT DOCUMENTS

WO    2010/127059    * 11/2010

OTHER PUBLICATIONS

Gaskell, "Electrospray: Principles and Practice." J. Mass. Spect., vol. 32, 677-688 (1997).

(Continued)

*Primary Examiner* — Maureen Wallenhorst
(74) *Attorney, Agent, or Firm* — Brown Rudnick LLP; Adam M. Schoen

(57) ABSTRACT

The invention generally relates to systems and methods for sample analysis. In certain embodiments, the invention provides a system for analyzing a sample that includes a probe including a material connected to a high voltage source, a device for generating a heated gas, and a mass analyzer.

21 Claims, 31 Drawing Sheets

(56) References Cited

U.S. PATENT DOCUMENTS

| | | | |
|---|---|---|---|
| 7,977,629 B2 * | 7/2011 | McEwen et al. | 250/288 |
| 8,294,892 B2 | 10/2012 | Sardashti et al. | |
| 2004/0011954 A1 | 1/2004 | Park | |
| 2005/0117864 A1 | 6/2005 | Dziekan et al. | |
| 2005/0247870 A9 | 11/2005 | Park | |
| 2006/0192107 A1 | 8/2006 | DeVoe et al. | |
| 2006/0200316 A1 | 9/2006 | Kanani et al. | |
| 2006/0249668 A1 | 11/2006 | Goldberg et al. | |
| 2007/0151232 A1 | 7/2007 | Dalla Betta et al. | |
| 2008/0067352 A1 * | 3/2008 | Wang | 250/288 |
| 2008/0128608 A1 | 6/2008 | Northen et al. | |
| 2008/0193772 A1 * | 8/2008 | Agroskin et al. | 428/421 |
| 2008/0272294 A1 | 11/2008 | Kovtoun | |
| 2009/0071834 A1 | 3/2009 | Hafeman et al. | |
| 2009/0090856 A1 | 4/2009 | Grant et al. | |
| 2009/0280300 A1 | 11/2009 | Craighead et al. | |
| 2010/0019143 A1 | 1/2010 | Dobson et al. | |
| 2010/0163722 A1 * | 7/2010 | Shiokawa et al. | 250/282 |
| 2011/0193027 A1 | 8/2011 | Mackenzie et al. | |
| 2012/0119079 A1 * | 5/2012 | Ouyang et al. | 250/282 |
| 2013/0112867 A1 | 5/2013 | Ouyang et al. | |

OTHER PUBLICATIONS

Lozano, et al. "Ionic Liquid Ion Sources: Characterization of Externally Wetted Emitters", Journal of Colloid and Interface Science 282 (2005) 415-421.

International Search Report and Written Opinion for PCT/US2010/032881 for International Searching Authority, mailed Aug. 4, 2010.

International Preliminary Report of Patentability for PCT/US2010/032881 from International Bureau, mailed Nov. 10, 2011.

* cited by examiner

Hydrocarbons, C44-C100
MXT®-1HT Sim Dist

SYSTEMS AND METHODS FOR SAMPLE ANALYSIS

RELATED APPLICATION

The present application is a 35 U.S.C. §371 national phase application of PCT international application number PCT/US11/67771, filed Dec. 29, 2011, which claims the benefit of and priority to U.S. provisional patent application Ser. No. 61/430,021, filed Jan. 5, 2011, the content of each of which is incorporated by reference herein in its entirety.

GOVERNMENT SUPPORT

This invention was made with government support under CHE0848650 awarded by National Science Foundation and DE-FG02-06ER15807 awarded by Department of Energy. The government has certain rights in the invention.

FIELD OF THE INVENTION

The invention generally relates to systems and methods for sample analysis.

BACKGROUND

Functional group chemistry is based on alkanes. This provides a pedagogical imperative for their characterization which complements the economic imperative of heavy alkane ("heavies") characterization. Amongst the spectroscopic methods, mass spectrometry has been connected particularly strongly to the petroleum industry, specifically to the analysis of hydrocarbon cracking products (Fisher et al., *Anal. Chem.* 1975, 47, 59). The first commercial mass spectrometers were used for this purpose and the influential method of chemical ionization and much early fundamental ion/molecule chemistry was developed by petroleum scientists (Field et al., *J. Am. Chem. Soc.* 1956, 5697; and Field et al., *J. Am. Chem. Soc.* 1957, 79, 2419). More recently, high resolution ion cyclotron resonance mass spectrometry (MS) has been applied to help elucidate the remarkable complexity of petroleum-derived materials using Kendrick mass defects to organize in a compact fashion the various functional group constituents of petroleum-derived samples (Qian et al., *Energ. Fuel.* 2001, 15, 492). Two groups of petroleum-derived compounds, the asphaltenes and the waxes, however, still provide particular difficulties in detailed characterization by MS and other methods (Pinkston et al., *Energy Fuels* 2009, 23, 5564; and Pomerantz et al., *J. Am. Chem. Soc.* 2008, 130, 7216).

SUMMARY

The invention generally relates to systems and methods for sample analysis. Systems and methods of the invention allow for mass spectral analysis of heavy alkanes, and thus allow for analysis of certain petroleum-derived compounds that could not previously be easily analyzed by mass spectrometry, such as waxes.

In certain aspects, the invention provides systems for analyzing a sample that include a probe including a material connected to a high voltage source, a device for generating a heated gas, and a mass analyzer. The material may be a porous material (e.g., paper, filter, paper or PVDF membrane) or a non-porous material (e.g., a metal such as aluminum). Further description of systems that utilize porous materials for ionization is provided in PCT/US10/32881 to Purdue Research Foundation and Wang et al., *Angew. Chem. Int. Ed.* 2010, 49, 877, the content of each of which is incorporated by reference herein in its entirety. In certain embodiments, the system operates under ambient conditions.

In certain embodiments, the heated gas is directed at the probe, for example the heated gas is directed at a tip of the probe. In other embodiments, the system further includes a chamber configured to encompass the probe and the device for generating the heated gas. In this embodiment, the gas within the chamber is heated and consequently heats the probe. Thus, the heated gas does not need to be directed at the probe. An exemplary gas is nitrogen. Due to the configuration of the system, the heated gas assists in ionizing the sample and participates in a chemical reaction with the sample, i.e., the heated gas participates in an ionic reaction to ionize the sample and also modifies the analyte. Generally, the ionizing and the chemical reaction occur simultaneously.

Exemplary porous materials include paper or PVDF membrane. An exemplary paper is filter paper. In particular embodiments, the probe is shaped to have a pointed tip. For example, in certain embodiments, the probe is composed of filter paper that is shaped as a triangular piece. Exemplary non-porous materials include metals, such as aluminum. In particular embodiments, the probe is shaped to have a pointed tip. For example, in certain embodiments, the probe is composed of aluminum that is shaped as a triangular piece.

The mass analyzer may be that of a bench-top mass spectrometer or a handheld mass spectrometer. Exemplary mass analyzers include a quadrupole ion trap, a rectalinear ion trap, a cylindrical ion trap, an ion cyclotron resonance trap, or an orbitrap.

In other aspects, the invention provides a method for analyzing a sample that involves contacting a sample to a material, applying high voltage and heat to the material to generate ions of an analyte in the sample that are expelled from the material, and analyzing the expelled ions. In certain embodiments, the method is performed under ambient conditions. In certain embodiments, analyzing involves providing a mass analyzer to generate a mass spectrum of analytes in the sample.

The sample may be any chemical or biological sample. The sample may be a liquid or a solid. In particular embodiments, the sample is a solid. In certain embodiments, the solid is a heavy alkane, such as a petroleum-derived compound. In particular embodiments, the petroleum-derived compound is a wax.

The heat may be produced by any method known in the art. In particular embodiments, the heat is produced from a heated gas. In certain embodiments, the heated gas is directed at the probe, for example the heated gas is directed at a tip of the probe. In other embodiments, the applying step of the method is conducted in an enclosed chamber, and thus the gas within the chamber is heated and consequently heats the probe. Thus, the heated gas does not need to be directed at the probe. An exemplary gas is nitrogen. In certain embodiments, the heated gas assists in ionizing the sample and participates in a chemical reaction with the sample, i.e., the heated gas participates in an ionic reaction to ionize the sample and also modifies the analyte. Generally, the ionization step and the chemical reaction occur simultaneously.

Another aspect of the invention provides methods for ionizing a sample involving applying high voltage and heat to a material to generate ions of an analyte in the sample.

Another aspect of the invention provides methods for analyzing a heavy alkane that involve obtaining a heavy alkane, and using a direct ambient ionization technique to analyze the heavy alkane. In particular embodiments, the heavy alkane is a solid. In certain embodiments, the heavy alkane is a component of a petroleum-derived compound. In particular embodiments, the heavy alkane is a wax.

Exemplary mass spectrometry techniques that utilize direct ambient ionization/sampling methods including desorption electrospray ionization (DESI; Takats et al., Science, 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), and electrospray-assisted laser desorption/ionization (ELDI; Shiea et al., J. Rapid Communications in Mass Spectrometry, 19:3701-3704, 2005). The content of each of these references in incorporated by reference herein in its entirety.

In particular embodiments, the direct ambient ionization technique involves contacting the heavy alkane to a material, applying high voltage and heat to the porous material to generate ions of an analyte in the heavy alkane that are expelled from the material, and analyzing the expelled ions. The material may be a porous material (e.g., paper, filter, paper or PVDF membrane) or a non-porous material (e.g., a metal such as aluminum). Further description of systems that utilize porous materials is provided in PCT/US10/32881 to Purdue Research Foundation and Wang et al., *Angew. Chem. Int. Ed.* 2010, 49, 877, the content of each of which is incorporated by reference herein in its entirety. In certain embodiments, analyzing involves providing a mass analyzer to generate a mass spectrum of analytes in the sample.

The heat may be produced by any method known in the art. In particular embodiments, the heat is produced from a heated gas. In certain embodiments, the heated gas is directed at the probe, for example the heated gas is directed at a tip of the probe. In other embodiments, the applying step of the method is conducted in an enclosed chamber, and thus the gas within the chamber is heated and consequently heats the probe. Thus, the heated gas does not need to be directed at the probe. An exemplary gas is nitrogen.

Other aspects of the invention provide methods for tracking carbon in the course of petroleum processing. Methods of the invention involve using a direct ambient ionization technique to generate ions of an analyte in a sample derived from petroleum processing, directing the ions into a mass analyzer, mass-separating the ions according to their mass, detecting the mass-separated ions from the sample, and utilizing the detected ions for determining the relative amounts of the various chemical forms of carbon in the sample.

In certain embodiments, the sample is a solid. In particular embodiments, the sample includes heavy alkanes. In particular embodiments, the sample is a wax.

In certain embodiments, the direct ambient ionization technique involves contacting the heavy alkane to a material, and applying high voltage and heat to the material to generate ions of an analyte in the sample that are expelled from the porous material. The material may be a porous material (e.g., paper, filter, paper or PVDF membrane) or a non-porous material (e.g., a metal such as aluminum). Further description of systems that utilize porous materials is provided in PCT/US10/32881 to Purdue Research Foundation and Wang et al., *Angew. Chem. Int. Ed.* 2010, 49, 877, the content of each of which is incorporated by reference herein in its entirety.

Another aspect of the invention provides methods for functionalizing an analyte in a sample that involve contacting a sample to a material, and applying high voltage and a heated gas to the material under conditions such that molecules of the heated gas modify an analyte in the sample, thereby functionalizing an analyte in the sample. The functionalized analyte may be converted into ions by the high voltage and the heated gas. The ions may be expelled from the material and analyzed. The ions may be collected and then analyzed or may be collected after analysis by, for example infrared spectrometry or mass spectrometry.

The material may be a porous material (e.g., paper, filter, paper or PVDF membrane) or a non-porous material (e.g., a metal such as aluminum). Further description of systems that utilize porous materials for ionization is provided in PCT/US10/32881 to Purdue Research Foundation and Wang et al., *Angew. Chem. Int. Ed.* 2010, 49, 877, the content of each of which is incorporated by reference herein in its entirety. In certain embodiments, the system operates under ambient conditions. In certain embodiments, the gas is nitrogen.

The sample may be a liquid or a solid. In particular embodiments, the sample is a solid. In certain embodiments, the solid is a heavy alkane, such as a petroleum-derived compound. In particular embodiments, the petroleum-derived compound is a wax.

DETAILED DESCRIPTION

Figure 1:
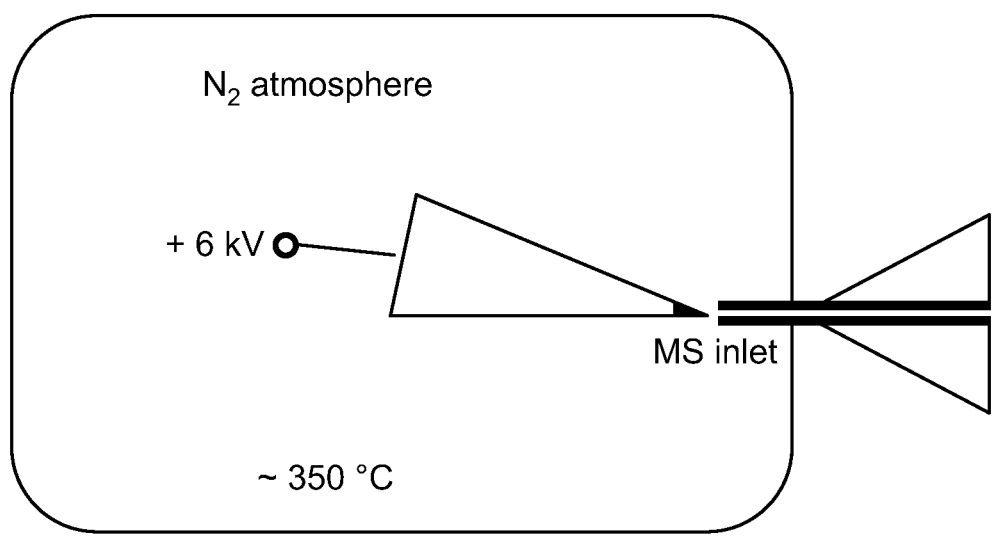
FIG. 1 provides an embodiment of systems of the invention.

Shown herein is alkane activation chemistry that forms the basis for an extremely simple yet robust method of generating unique ions and recording mass spectra of heavy alkanes, such as waxes, cycloalkanes, and long chain functionalized alkane based compounds. An exemplary system set-up is shown in FIG. 1. This figure shows an exemplary system of the invention that includes a chamber that encompasses a probe, a heat generating device, and an MS inlet. Other system configures are possible and are described herein. Using such a system, high mass waxes can be ionized by floating dry wax-impregnated paper at a high potential in a hot nitrogen atmosphere and sucking the generated ions into a mass spectrometer. Nitrogen ion insertion into the activated alkane gives $[M+N]^+$ ions. Thus, the heated gas assists in ionizing the sample and participates in a chemical reaction with the sample, i.e., the heated gas participates in an ionic reaction to ionize the sample and also modifies the analyte. Generally, the ionizing and the chemical reaction occur simultaneously.

Figure 2:
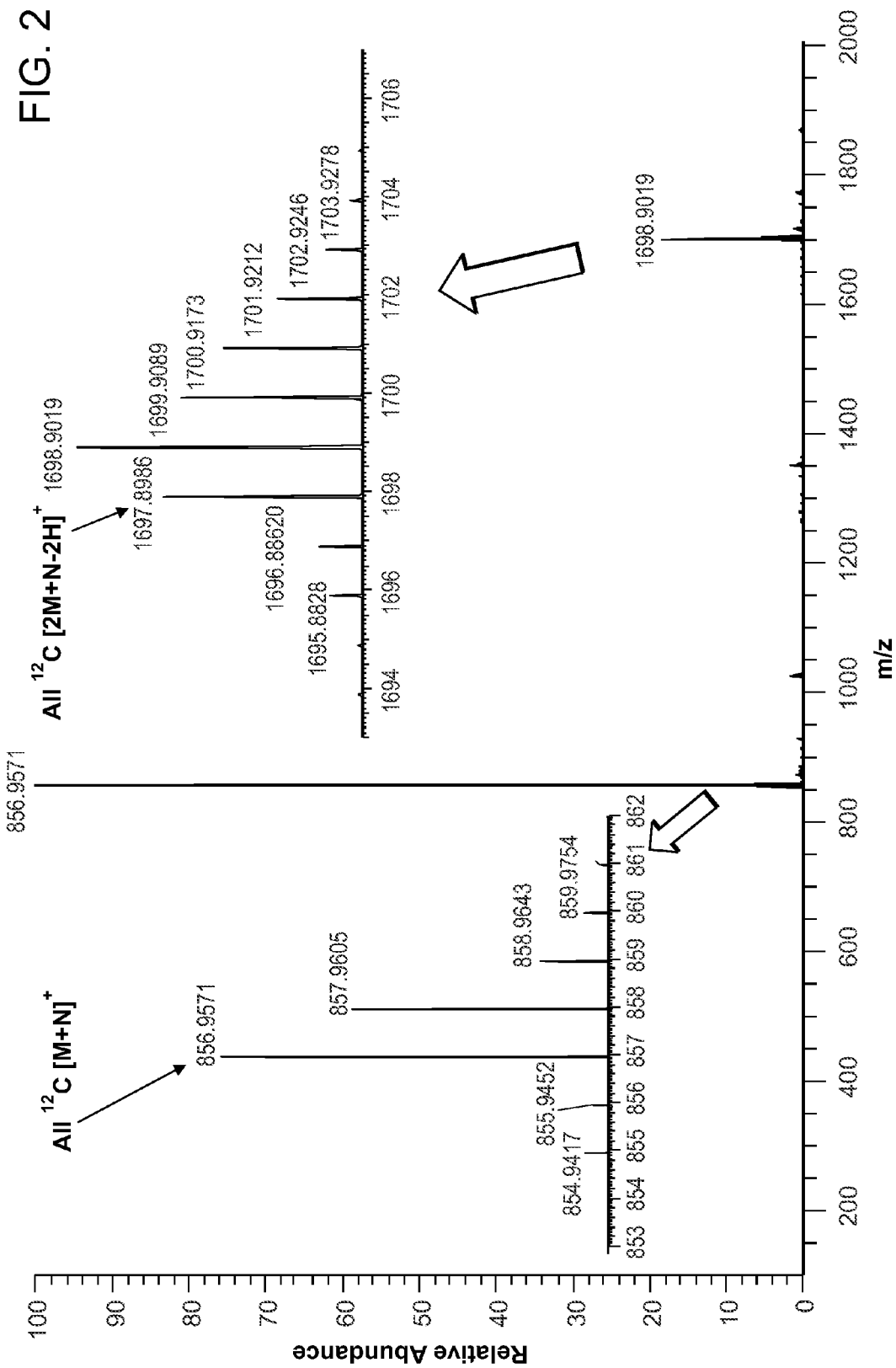
FIG. 2 is a mass spectrum of wax n-$C_{60}H_{122}$, $N_2$ atmosphere, 325° C., 6 kV, using LTQ Orbitrap and showing expanded $[M+N]^+$ and $[2M+N-2H]^+$ regions, $M=^{12}C_{60}{}^{1}H_{122}$.

The wax $C_{60}H_{122}$ is deposited as the solid (or from solution or as the sublimate) onto the tip of a piece of filter paper cut into a triangle. A potential of a few kV is applied to the paper in a heated nitrogen atmosphere, and a spectrum such as that shown in FIG. 2 is recorded. The spectrum of the $C_{60}$ wax is dominated (excluding carbon isotopes) by just two ions: $[M+14]^+$ and $[2M+12]^+$, where M is the monoisotopic molecular weight of the compound, i.e. 842.9546 Da in the case of $C_{60}H_{122}$. Exact mass measurements made using an LTQ Orbitrap instrument showed that the major ions have the formula $[M+N]^+$ for which the expected value is m/z 856.9577; the measured value of m/z 856.957(2) agrees with this value but excludes $[M+CH_2]^+$ which requires m/z 856.9703. Similarly, the main dimeric ion, $[2M+12]^+$, has the formula $[2M+N-2H]^+$ with a measured mass of 1697.896(8) and an expected mass of 1697.8967. The same nitrogen incorporation was observed for the $C_{40}$ and $C_{50}$ waxes as shown in Table 1 below.

TABLE 1

| Alkane | M (all $^{12}C$, $^{1}H$) | M + N | M + $CH_2$ | M + O – 2H | Observed | 2M + N – 2H | Observed |
|---|---|---|---|---|---|---|---|
| Tetracontane, $C_{40}H_{82}$ | 562.64162 | 576.64469 | 576.65727 | 576.62088 | 576.64459 | 1137.27066 | 1137.27185 |
| Pentacontane, $C_{50}H_{102}$ | 702.79811 | 716.80118 | 716.81376 | 716.77738 | 716.8000 | 1417.58364 | 1417.5807 |
| Hexacontane, $C_{60}H_{122}$ | 842.94560 | 856.95768 | 856.97025 | 856.93387 | 856.9571 | 1697.89663 | 1697.8986 |

To explore the applicability of this chemistry in analyzing molecular weight distributions of heavy alkanes, a commercial heavy wax standard Polywax 1000 (Restek Corporation, Bellefonte, Pa.) was examined. The main peak envelope corresponds to the saturated alkanes. For example, the ion at nominal m/z 1558 corresponds to the alkane with carbon number $C_{110}$ (average chemical mass of the N-adduct 1558.95; exact mass of $^{12}C$-isotope 1557.74, measured mass 1557.7). The isotopic distribution (FIG. 3B) agrees well with calculation for $C_{110}H_{222}$. The molecular weight distribution in FIG. 3 extends to at least m/z 1895, which corresponds to the $C_{134}H_{270}$ saturated hydrocarbon. The m/z 1165.33 peak, corresponding to $C_{82}H_{166}$, is the most abundant. These observations are consistent with the manufacturer's data (See FIG. 8 and Table 2 below).

TABLE 2

| ASTM D5307 Crude oil qualitative standard | | | |
|---|---|---|---|
| | molecular weight | M – 1 | M + 14 |
| Decane | 6.25% | 142 | 141 | 156 |
| Undecane | 6.25% | 156 | 155 | 170 |
| Dodecane | 6.25% | 170 | 169 | 184 |
| Tridecane | 6.25% | 184 | 183 | 198 |
| Tetradecane | 6.25% | 198 | 197 | 212 |
| Pentadecane | 6.25% | 212 | 211 | 226 |

TABLE 2-continued

ASTM D5307 Crude oil qualitative standard

|  | molecular weight | M − 1 | M + 14 |
|---|---|---|---|
| Hexadecane | 6.25% | 226 | 225 | 240 |
| Heptadecane | 6.25% | 240 | 239 | 254 |
| Octadecane | 6.25% | 254 | 253 | 268 |
| Eicosane | 6.25% | 282 | 281 | 296 |
| Tetracosane | 6.25% | 338 | 337 | 352 |
| Octacosane | 6.25% | 394 | 393 | 408 |
| Dotriacontane | 6.25% | 450 | 449 | 464 |
| Hexatriacontane | 6.25% | 506 | 505 | 520 |
| Tetracontane | 6.25% | 562 | 561 | 576 |
| Tetratetracontane | 6.25% | 618 | 617 | 632 |

Figure 3A:
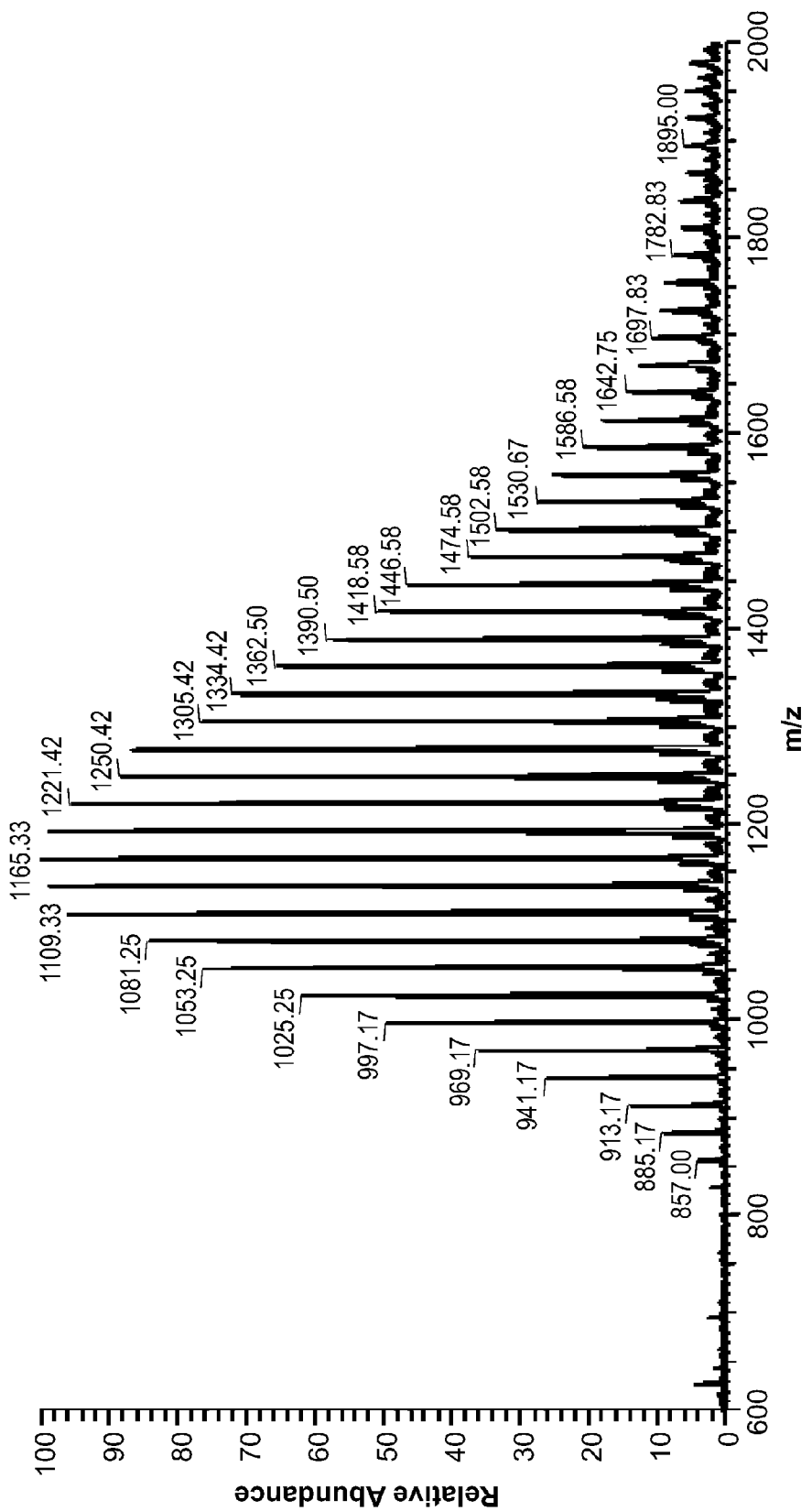
FIGS. 3A and 3B are mass spectra recorded from filter paper in $N_2$ atmosphere (a) standard Polywax 1000 sample; and (b) isotopic distribution for the $C_{110}$ peaks compared to calculated isotopic distribution of $C_{110}H_{222}N$.
Figure 3B:
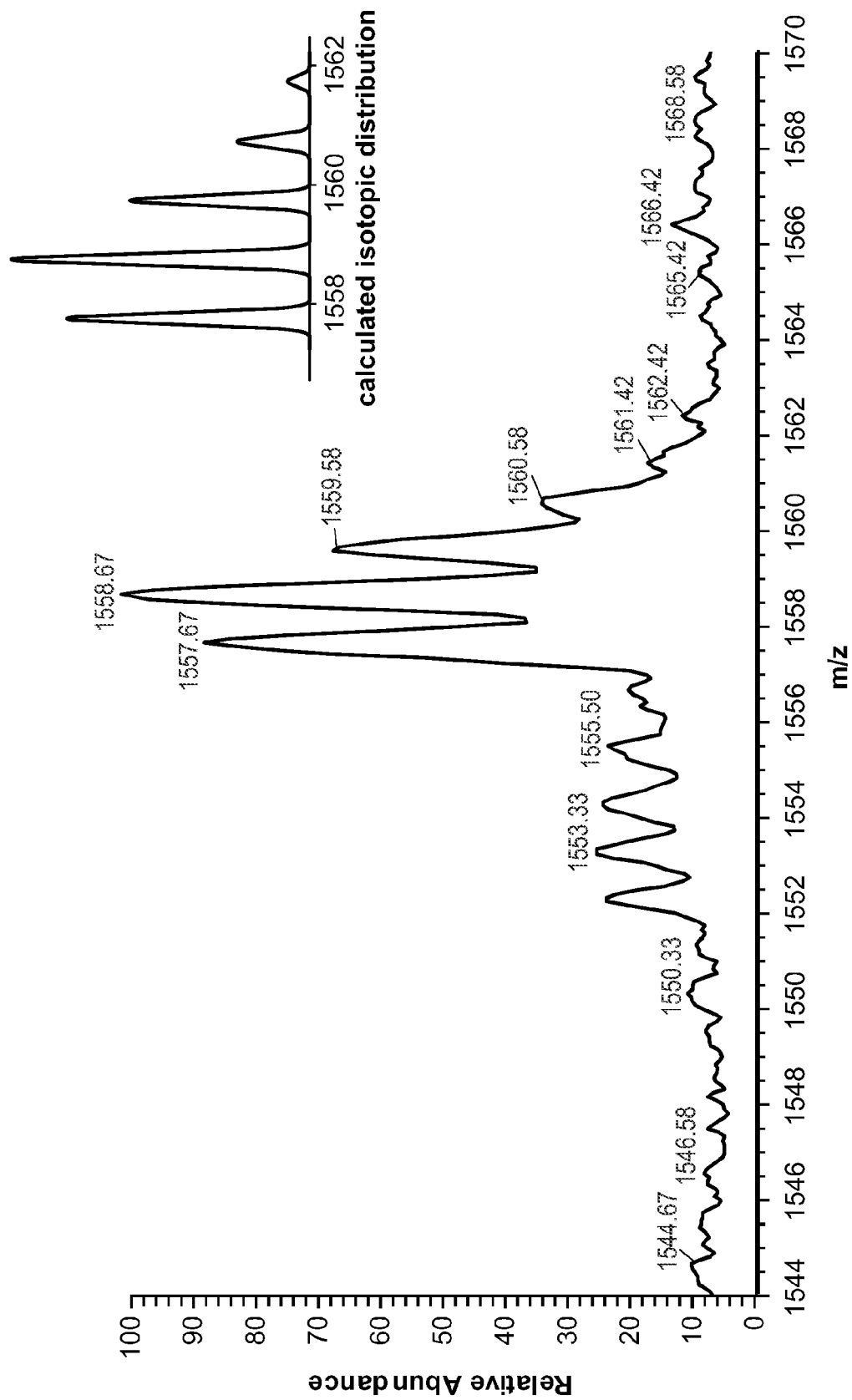

In addition to the [M+N]$^+$ series, an ion corresponding to [(M'+23]$^+$ is evident from the isotopic envelope (M' is the alkane with two fewer carbon atoms, FIG. 3B) as well as in the molecular weight profile (FIG. 3A).

Optimized conditions for alkane analysis (Examples herein) were used to produce the data shown in FIGS. 2 and 3. The experiment was done in a N$_2$ atmosphere in an isolated chamber normally used for atmospheric pressure chemical ionization, electrically heated to 80-500° C., with a potential of 6 kV applied to the paper holding the sample. Two other sets of experimental conditions were also explored (Example 2 herein). In one, the sample again was ionized from paper, but was heated in open air with a heat gun while supplying the high voltage. In the other alternative, which followed earlier work on transmission mode desorption electrospray ionization (DESI; Chipuka et al., *J. Am. Soc. Mass Spectrom.* 2008, 19, 1612), the sample was placed on a stainless steel mesh, a potential of 1.5-2 kV was applied to a needle in front of the mesh, and a stable arc discharge established. Summarizing the data from the three types of experiments: (i) Paper spray in a N$_2$ chamber heated up to 400° C. (preferably 100° C. to 150° C., is successful for larger n-alkanes (≥C28); it gives [M+N]$^+$ and [M+N-2H]$^+$ as well as dimeric ions [2M+N—H$_y$]$^+$ where y is 1 and 4. (ii) Paper spray in the open air at 300° C. is effective for medium-sized alkanes and gives mainly [M−H]$^+$, accompanied by various oxygenated species. (iii) Mesh discharge in open air, with heating, was successful for light and medium-sized hydrocarbons as well as other hydrocarbons. More detailed information is provided in the Examples herein.

Because it proved easier to control conditions to produce [M+N]$^+$ instead of [M−H]$^+$ ions, most attention was focused on those species. However, both ions are formed by highly unusual chemical processes. The [M−H]$^+$ ions appear not to be formed by ion/molecule reactions but rather to involve a field ionization process (Examples herein). Following Rollgen (*Ber. Bunsenges. Phys. Chem.* 1971, 75, 988) the origin of [M−H]$^+$ was tentatively ascribed to field desorption with proton transfer to the emitter surface (the paper or metal). See Pirkl (Analytical and Bioanalytical Chemistry, 2010, 397(8), 3311). The observation of traces of molecular radical cations (M$^+$·) suggests that a minor component of ionization occurs by simple field ionization. The most remarkable products are [M+N]$^+$ and [2M+N−2H]$^+$. The major reaction, leading to the former, formally involves net N$^+$ addition to an alkane, as shown in FIGS. 2, 3A and 3B, 9, and 10. This represents an unprecedented substitution into the C—C (or C—H) bond of an alkane.

Figure 4A:
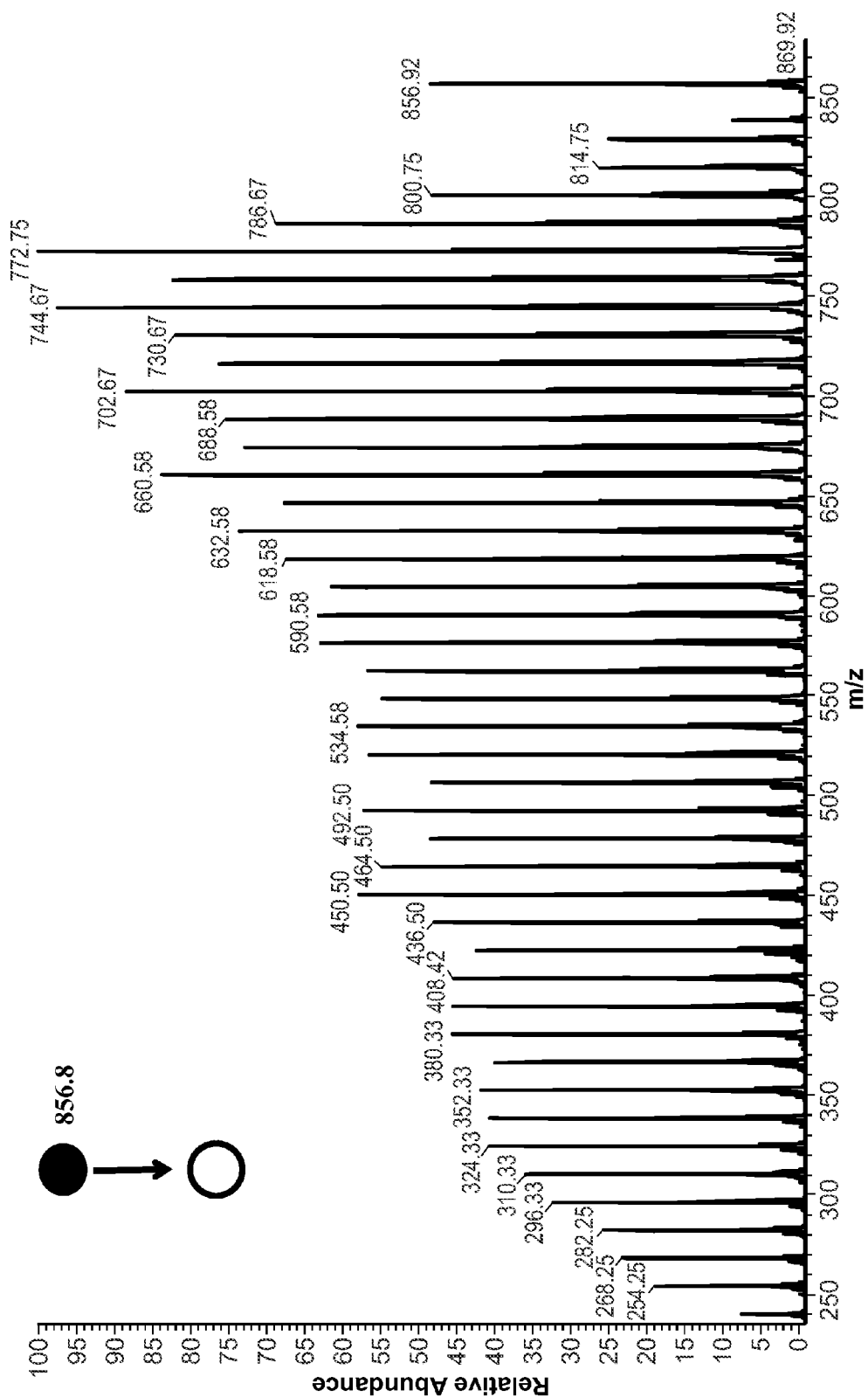
FIGS. 4A and 4B show (a) MS/MS and (b) $MS^3$ product ion spectra showing all fragments (above the low mass cut-off) generated via the sequence $[M+N]^+$ (m/z 856.8)→$C_{19}H_{40}N^+$ (m/z 282.2). Note in (a) the complete set of alkene eliminations and in (b) the loss of nitrogen to give monounsaturated alkenyl cations.
Figure 4B:
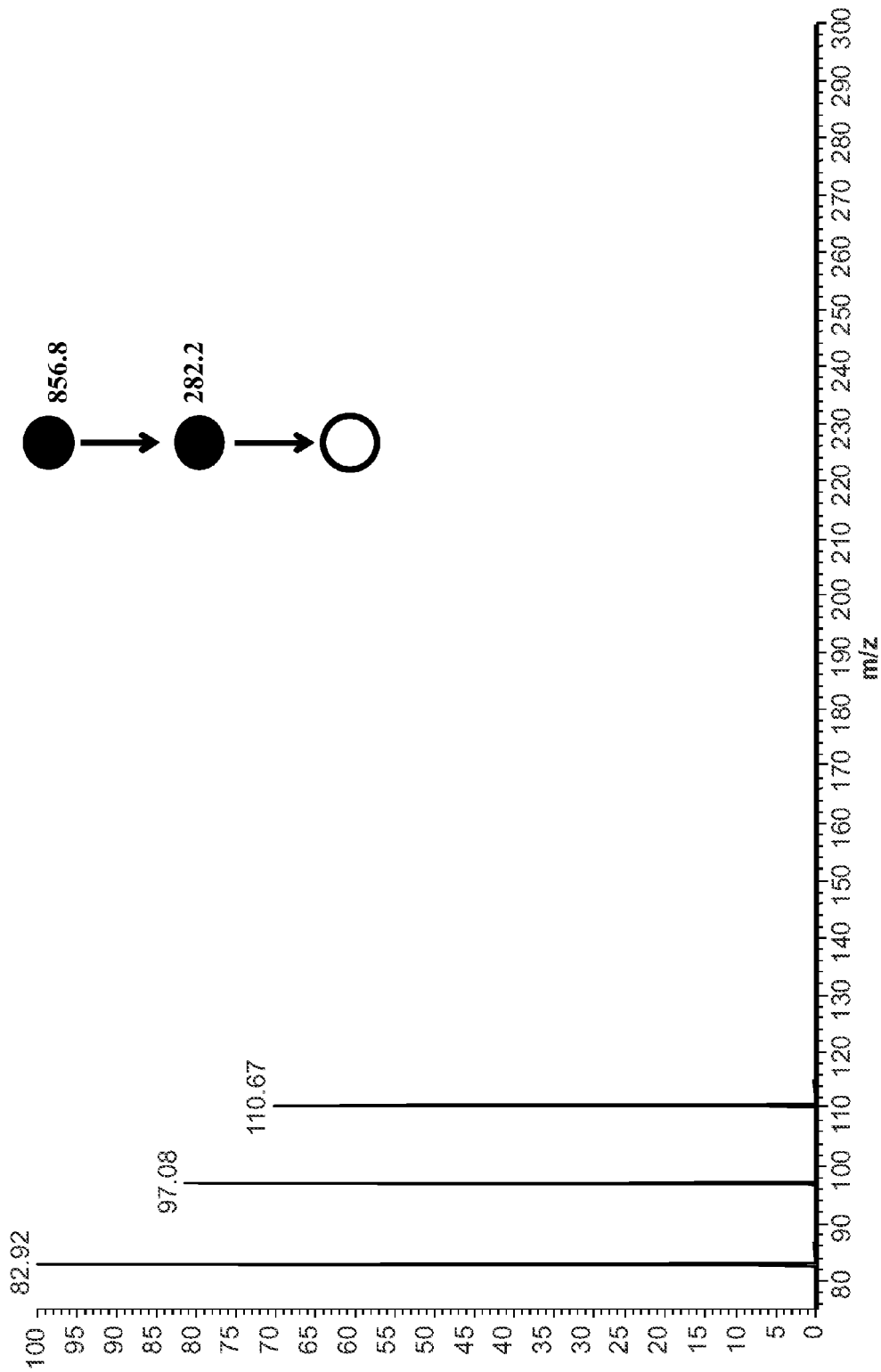
Figure 5:
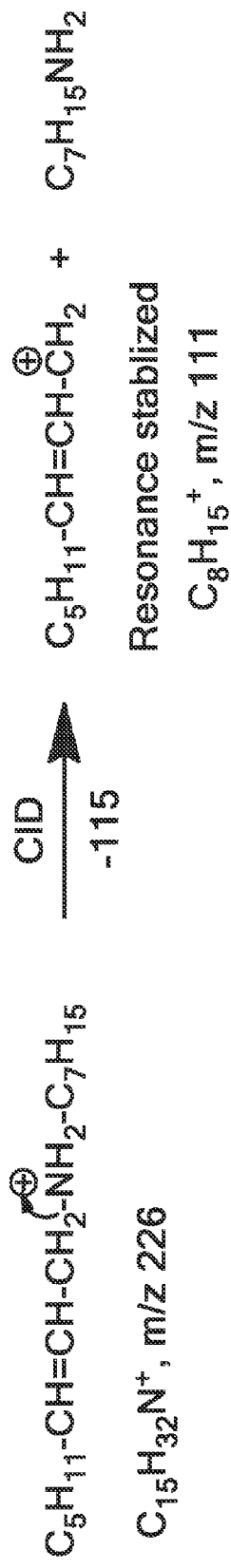
FIG. 5 shows a reaction scheme of a proposed CID fragmentation mechanism leading to alkyl amine elimination with formation of alkenyl cations in the $MS^3$ spectra.

Multiple stage experiments (MS/MS and MS$^3$) provided information on the nature of the [M+N]$^+$ ions. The MS/MS data displayed mainly alkene eliminations (FIG. 4A), a highly characteristic fragmentation for long chain alkyl compounds, whether functionalized or not. The MS$^3$ data provided access to lower mass ions and this showed additional surprising results typified by the data in FIG. 4B. Further fragmentation of any of the ions generated by alkene loss from the [M+N]$^+$ precursor (i.e. of its lower homologs [M+N]$^+$) occurs by loss of size-specific alkyl amines to give alkenyl cations with a narrow range of small carbon numbers. The MS$^3$ data indicate the position of nitrogen insertion, showing a strong preference for C-6 to C-9 insertion. A possible mechanism for the fragmentation is shown as FIG. 5 for one representative MS$^3$ spectrum (that involving the intermediate ion of m/z 226).

Without being limited by any theory or mechanism of action, these data suggest nitrogen insertion into C—C bonds that lie near but not at the ends of the n-alkane chain. The site specificity of nitrogen insertion suggests an ionic rather than a free radical N-donor (such as the azide radical; Continetti et al., *J. Chem. Phys.* 1993, 99, 2616). The main ions generated in an atmospheric pressure nitrogen discharge are N$_3$$^+$ and N$_4$$^+$. (Dzidic et al., *Anal. Chem.* 1976, 48, 1763). This leads to the proposal that the primary reaction with alkanes involves N$^+$ insertion from an azide ion with dinitrogen elimination.

The role of the high voltage is not simply to generate a corona discharge in the nitrogen atmosphere. Such discharges are often generated and there is no associated reactivity. The nitrogen may also be participating in a chemical reaction with the analyte. The nitrogen acts as a chemical ionization agent, and the alkane is activated by the electric filed, allowing it to undergo reaction with the ionized nitrogen. It seems likely that the presence of a high electric field at the point of the material where the sample is placed is responsible for insertion of the nitrogen atomic ion; viz. the process is not purely a gas phase reaction. In preferred embodiments, the wax is placed at the tip of the material as it is not mobile nor is solvent used to mobilize it.

Figure 6:
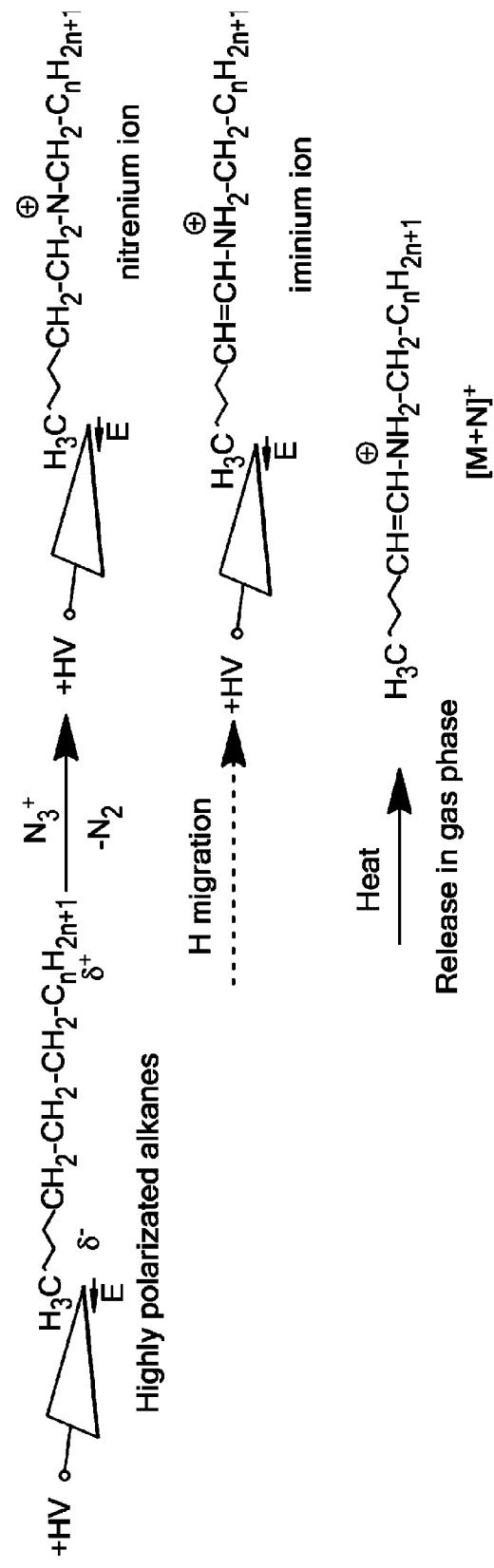
FIG. 6 shows a reaction scheme of a tentative mechanism for atomic nitrogen ion insertion into alkanes on an electrically floated paper substrate. The alkanes are activated by the applied potential.
Figure 7:
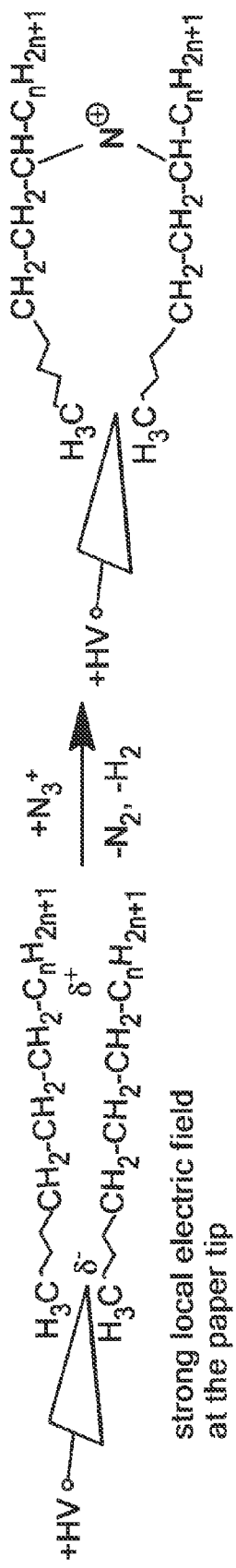
FIG. 7 shows a reaction scheme for the first steps in formation of dimeric ions, including $[2M+N-2H]^+$.

Without being limited by any theory or mechanism of action, it is tentatively proposed that the non-volatile waxes are field-activated while physisorbed to the substrate where they are strongly polarized by the strong terminal electric fields. It is suggested further that the field-activated alkanes react with the N-donor, N$_3$$^+$. Evidence for the role of the electric field comes from these facts (i) the reaction does not occur with other compounds tested—for example, peptides, cholesterol, cocaine etc. (ii) the reaction is favoured in heavy alkanes over light alkanes (this may contribute to the tailing off of the envelope at lower mass in FIG. 3A) (iii) the occurrence of dimeric ions supports a surface-mediated mechanism. We propose that the physisorbed alkane molecule is polarized by the charge on the paper, leading to induced charges in the molecule as represented in FIG. 6. In certain instances, dimeric ions may be formed. See FIG. 7.

The favoured site of azide cation attack will be at the end of the molecule closest to the paper due the magnitude of the induced charge in the alkane molecule (Lorquet, *Mol. Phys.* 1965, 9, 101; and Lorquet, *J. Phys. Chem.* 1969, 73, 463). Steric factors probably contribute to the favoured reaction site being some distance from the chain terminus. There appear to be no thermochemical data on the azide cation and no instances of its ion/molecule reactivity. The closest analogs to N$^+$ insertion into an alkane C—H or C—C bond involve light metal gas-phase atomic ion chemistry (Schwarz et al., *Pure Appl. Chem.* 2000, 72, 2319; and Gord et al., *J. Chem. Phys.* 1989, 91, 7535). Note that the intermediate generated in the proposed C—C insertion reaction is a nitrenium ion, a highly reactive class of intermediates of considerable current interest (Novak et al., *J. Phys. Org. Chem.* 1998, 11, 71).

Figure 11:
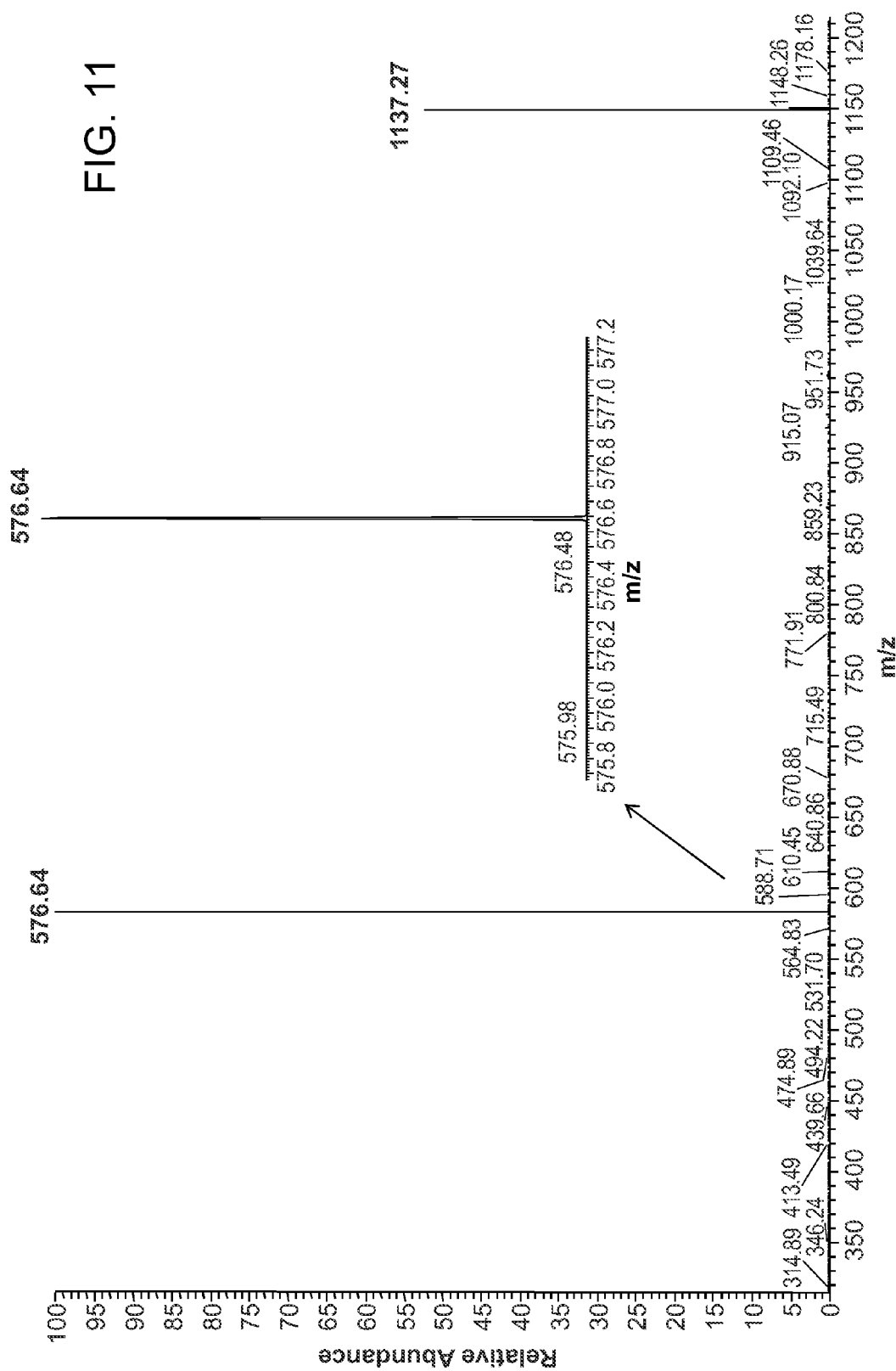
FIG. 11 is an MS/MS of $[2M+N-2H]^+$ ion of $C_{40}H_{82}$ alkane. The fragment is monoisotopic because the precursor ion is isolated at unit resolution.
Figure 12:
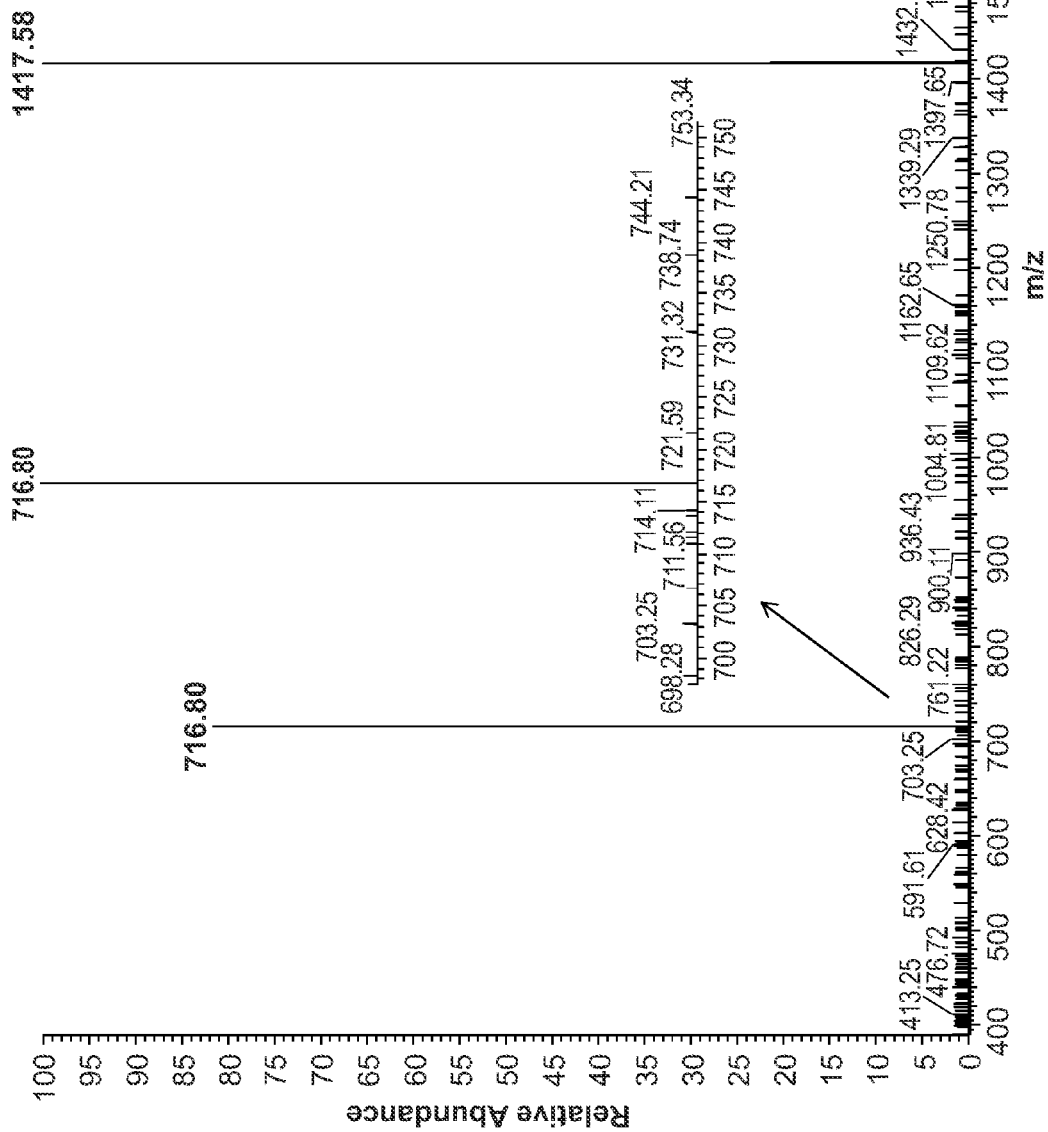
FIG. 12 is an MS/MS of $[2M+N-2H]^+$ ion of $C_{50}H_{102}$ alkane. The fragment is monoisotopic because the precursor ion is isolated at unit resolution.
Figure 13:
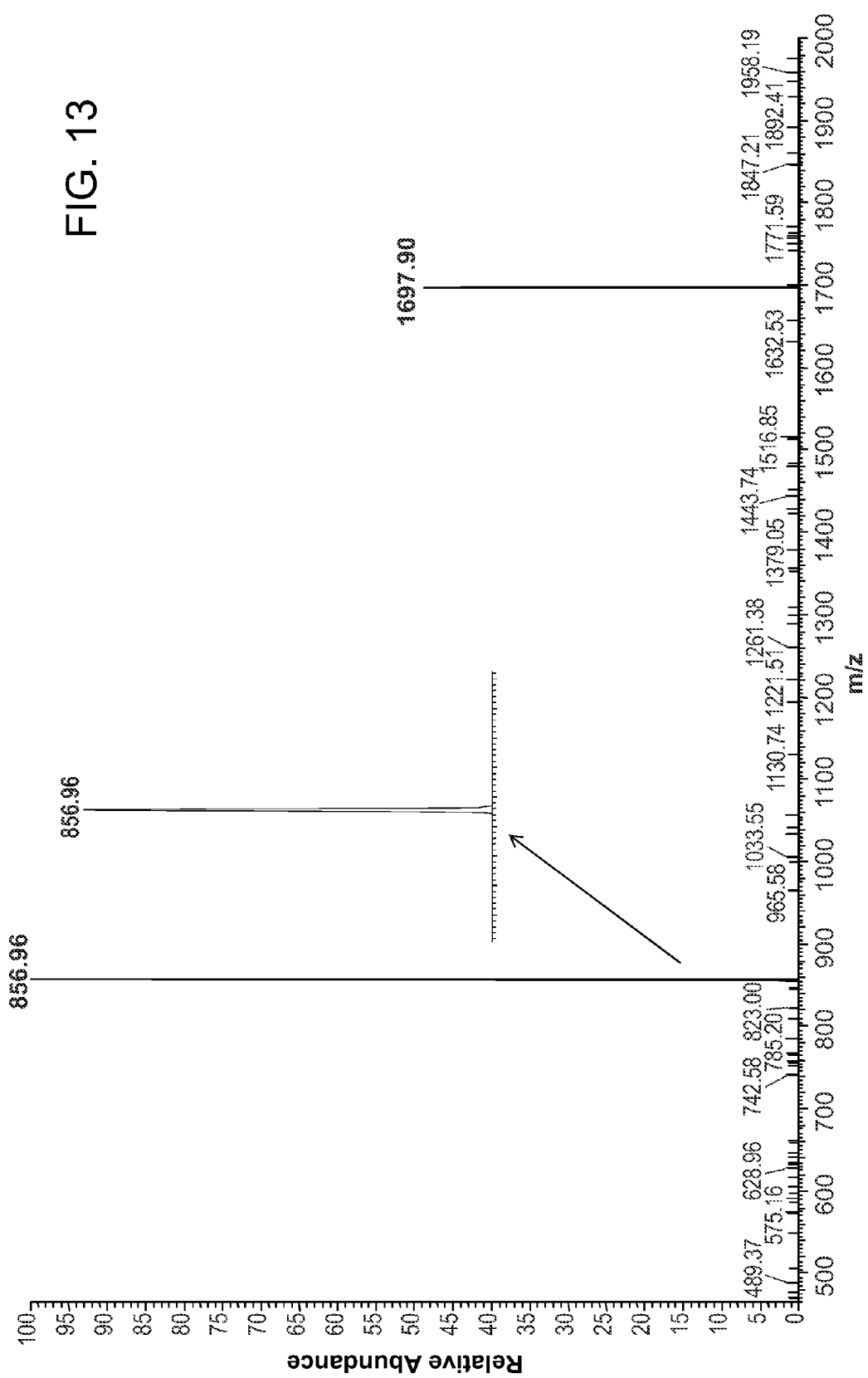
FIG. 13 is an MS/MS of $[2M+N-2H]^+$ ion of $C_{60}H_{122}$ alkane. The fragment is monoisotopic because the precursor ion is isolated at unit resolution.

MS/MS data on the dimeric ions (FIGS. 11-13) provide support for the field-activation mechanism proposed above. Interchain $N^+$ insertion with $H_2$ elimination to give a cross linked nitrenium ion is proposed to be responsible for formation of the dimer ions. This reaction is proposed to be followed by rearrangement to a stable ammonium adduct which fragments upon activation with alkene elimination to form a lower mass $[M+N]^+$ product.

It has been argued that the effective utilization of petroleum resources requires tracking carbon through the various chemical forms that it takes in the course of petroleum processing. This complex task, referred to as structure-oriented lumping (Jaffe et al., *Ind. Eng. Chem. Res.* 2005, 44, 9840) involves monitoring the 'carbon budget' and requires significant resources in terms of analytical methodology which are justified by the economic value of the knowledge acquired. The difficulty of analyzing high molecular weight alkanes by mass spectrometry is an impediment in full implementation of this task. These compounds can be ionized by two methods: that commonly used is the venerable field desorption (FD) method. This manually intensive method requires that a solution of the sample be dropped onto a fine dendritic emitter to which a potential is applied as it is heated in vacuum to create ions. The alternative method is Amirav's elegant molecular beam electron ionization method (Granota et al., *Int. J. Mass Spectrom.* 2005, 244, 15). Both methods give reproducible data but both involve ionization in vacuum and so lack the simplicity of the procedure described here. It seems likely that the $N^+$ insertion methodology described in this paper will have complementary properties and practical utility.

Collection of Ions

Systems and methods for collecting ions that have been analyzed by a mass spectrometer are shown in Cooks, (U.S. Pat. No. 7,361,311), the content of which is incorporated by reference herein in its entirety. Generally, the preparation of microchips arrays of molecules first involves the ionization of analyte molecules in the sample (solid or liquid). The molecules can be ionized by any of the methods discussed above. The ions are then separated based on their mass/charge ratio or their mobility or both their mass/charge ratio and mobility. For example, the ions can be accumulated in an ion storage device such as a quadrupole ion trap (Paul trap, including the variants known as the cylindrical ion trap and the linear ion trap) or an ion cyclotron resonance (ICR) trap. Either within this device or using a separate mass analyzer (such as a quadrupole mass filter or magnetic sector or time of flight), the stored ions are separated based on mass/charge ratios. Additional separation might be based on mobility using ion drift devices or the two processes can be integrated. The separated ions are then deposited on a microchip or substrate at individual spots or locations in accordance with their mass/charge ratio or their mobility to form a microarray.

To achieve this, the microchip or substrate is moved or scanned in the x-y directions and stopped at each spot location for a predetermined time to permit the deposit of a sufficient number of molecules to form a spot having a predetermined density. Alternatively, the gas phase ions can be directed electronically or magnetically to different spots on the surface of a stationary chip or substrate. The molecules are preferably deposited on the surface with preservation of their structure, that is, they are soft-landed. Two facts make it likely that dissociation or denaturation on landing can be avoided. Suitable surfaces for soft-landing are chemically inert surfaces that can efficiently remove vibrational energy during landing, but which will allow spectroscopic identification. Surfaces which promote neutralization, rehydration or having other special characteristics might also be used for protein soft-landing.

Generally, the surface for ion landing is located behind the detector assembly of the mass spectrometer. In the ion detection mode, the high voltages on the conversion dynode and the multiplier are turned on and the ions are detected to allow the overall spectral qualities, signal-to-noise ratio and mass resolution over the full mass range to be examined. In the ion-landing mode, the voltages on the conversion dynode and the multiplier are turned off and the ions are allowed to pass through the hole in the detection assembly to reach the landing surface of the plate (such as a gold plate). The surface is grounded and the potential difference between the source and the surface is 0 volts.

An exemplary substrate for soft landing is a gold substrate (20 mm×50 mm, International Wafer Service). This substrate may consist of a Si wafer with 5 nm chromium adhesion layer and 200 nm of polycrystalline vapor deposited gold. Before it is used for ion landing, the substrate is cleaned with a mixture of $H_2SO_4$ and $H_2O_2$ in a ratio of 2:1, washed thoroughly with deionized water and absolute ethanol, and then dried at 150° C. A Teflon mask, 24 mm×71 mm with a hole of 8 mm diameter in the center, is used to cover the gold surface so that only a circular area with a diameter of 8 mm on the gold surface is exposed to the ion beam for ion soft-landing of each mass-selected ion beam. The Teflon mask is also cleaned with 1:1 MeOH:$H_2O$ (v/v) and dried at elevated temperature before use. The surface and the mask are fixed on a holder and the exposed surface area is aligned with the center of the ion optical axis.

Any period of time may be used for landing of the ions. Between each ion-landing, the instrument is vented, the Teflon mask is moved to expose a fresh surface area, and the surface holder is relocated to align the target area with the ion optical axis. After soft-landing, the Teflon mask is removed from the surface.

In another embodiment a linear ion trap can be used as a component of a soft-landing instrument. Ions travel through a heated capillary into a second chamber via ion guides in chambers of increasing vacuum. The ions are captured in the linear ion trap by applying suitable voltages to the electrodes and RF and DC voltages to the segments of the ion trap rods. The stored ions can be radially ejected for detection. Alternatively, the ion trap can be operated to eject the ions of selected mass through the ion guide, through a plate onto the microarray plate. The plate can be inserted through a mechanical gate valve system without venting the entire instrument.

The advantages of the linear quadrupole ion trap over a standard Paul ion trap include increased ion storage capacity and the ability to eject ions both axially and radially. Linear ion traps give unit resolution to at least 2000 Thomspon (Th) and have capabilities to isolate ions of a single mass/charge ratio and then perform subsequent excitation and dissociation in order to record a product ion MS/MS spectrum. Mass analysis will be performed using resonant waveform methods. The mass range of the linear trap (2000 Th or 4000 Th but adjustable to 20,000 Th) will allow mass analysis and soft-landing of most molecules of interest. In the soft-landing instrument described above the ions are introduced axially into the mass filter rods or ion trap rods. The ions can also be radially introduced into the linear ion trap.

Methods of operating the above described soft-landing instruments and other types of mass analyzers to soft-land ions of different masses at different spots on a microarray are now described. The ions of the functionalized analyte from the sample are introduced into the mass filter. Ions of selected mass-to-charge ratio will be mass-filtered and soft-landed on the substrate for a period of time. The mass-filter settings then will be scanned or stepped and corresponding movements in the position of the substrate will allow deposition of the ions at defined positions on the substrate.

The ions can be separated in time so that the ions arrive and land on the surface at different times. While this is being done the substrate is being moved to allow the separated ions to be deposited at different positions. A spinning disk is applicable, especially when the spinning period matches the duty cycle of the device. The applicable devices include the time-of-flight and the linear ion mobility drift tube. The ions can also be directed to different spots on a fixed surface by a scanning electric or magnetic fields.

In another embodiment, the ions can be accumulated and separated using a single device that acts both as an ion storage device and mass analyzer. Applicable devices are ion traps (Paul, cylindrical ion trap, linear trap, or ICR). The ions are accumulated followed by selective ejection of the ions for soft-landing. The ions can be accumulated, isolated as ions of selected mass-to-charge ratio, and then soft-landed onto the substrate. Ions can be accumulated and landed simultaneously. In another example, ions of various mass-to-charge ratios are continuously accumulated in the ion trap while at the same time ions of a selected mass-to-charge ratio can be ejected using SWIFT and soft-landed on the substrate.

In a further embodiment of the soft-landing instrument ion mobility, is used as an additional (or alternative) separation parameter. As before, ions are generated by a suitable ionization source, such as those described herein. The ions are then subjected to pneumatic separation using a transverse air-flow and electric field. The ions move through a gas in a direction established by the combined forces of the gas flow and the force applied by the electric field. Ions are separated in time and space. The ions with the higher mobility arrive at the surface earlier and those with the lower mobility arrive at the surface later at spaces or locations on the surface.

The instrument can include a combination of the described devices for the separation and soft-landing of ions of different masses at different locations. Two such combinations include ion storage (ion traps) plus separation in time (TOF or ion mobility drift tube) and ion storage (ion traps) plus separation in space (sectors or ion mobility separator).

It is desirable that the structure of the analyte be maintained during the soft-landing process. On such strategy for maintaining the structure of the analyte upon deposition involves keeping the deposition energy low to avoid dissociation or transformation of the ions when they land. This needs to be done while at the same time minimizing the spot size. Another strategy is to mass select and soft-land an incompletely desolvated form of the ionized molecule. Extensive hydration is not necessary for molecules to keep their solution-phase properties in gas-phase. Hydrated molecular ions can be formed by electrospray and separated while still "wet" for soft-landing. The substrate surface can be a "wet" surface for soft-landing, this would include a surface with as little as one monolayer of water. Another strategy is to hydrate the molecule immediately after mass-separation and prior to soft-landing. Several types of mass spectrometers, including the linear ion trap, allow ion/molecule reactions including hydration reactions. It might be possible to control the number of water molecules of hydration. Still further strategies are to deprotonate the mass-selected ions using ion/molecule or ion/ion reactions after separation but before soft-landing, to avoid undesired ion/surface reactions or protonate at a sacrificial derivatizing group which is subsequently lost.

Different surfaces are likely to be more or less well suited to successful soft-landing. For example, chemically inert surfaces which can efficiently remove vibrational energy during landing may be suitable. The properties of the surfaces will also determine what types of in situ spectroscopic identification are possible. The ions can be soft-landed directly onto substrates suitable for MALDI. Similarly, soft-landing onto SERS-active surfaces should be possible. In situ MALDI and secondary ion mass spectrometry can be performed by using a bi-directional mass analyzer such as a linear trap as the mass analyzer in the ion deposition step and also in the deposited material analysis step.

In another embodiment, ions may be collected in the ambient environment (ambient pressure but still under vacuum) without mass analysis (See Examples herein). The collected ions may then be subsequently analyzed by any suitable technique, such as infrared spectrometry or mass spectrometry.

INCORPORATION BY REFERENCE

Any and all references and citations to other documents, such as patents, patent applications, patent publications, journals, books, papers, web contents, that have been made throughout this disclosure are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Example 1

Analysis of Alkanes Using Mass Spectrometry

Figure 8:
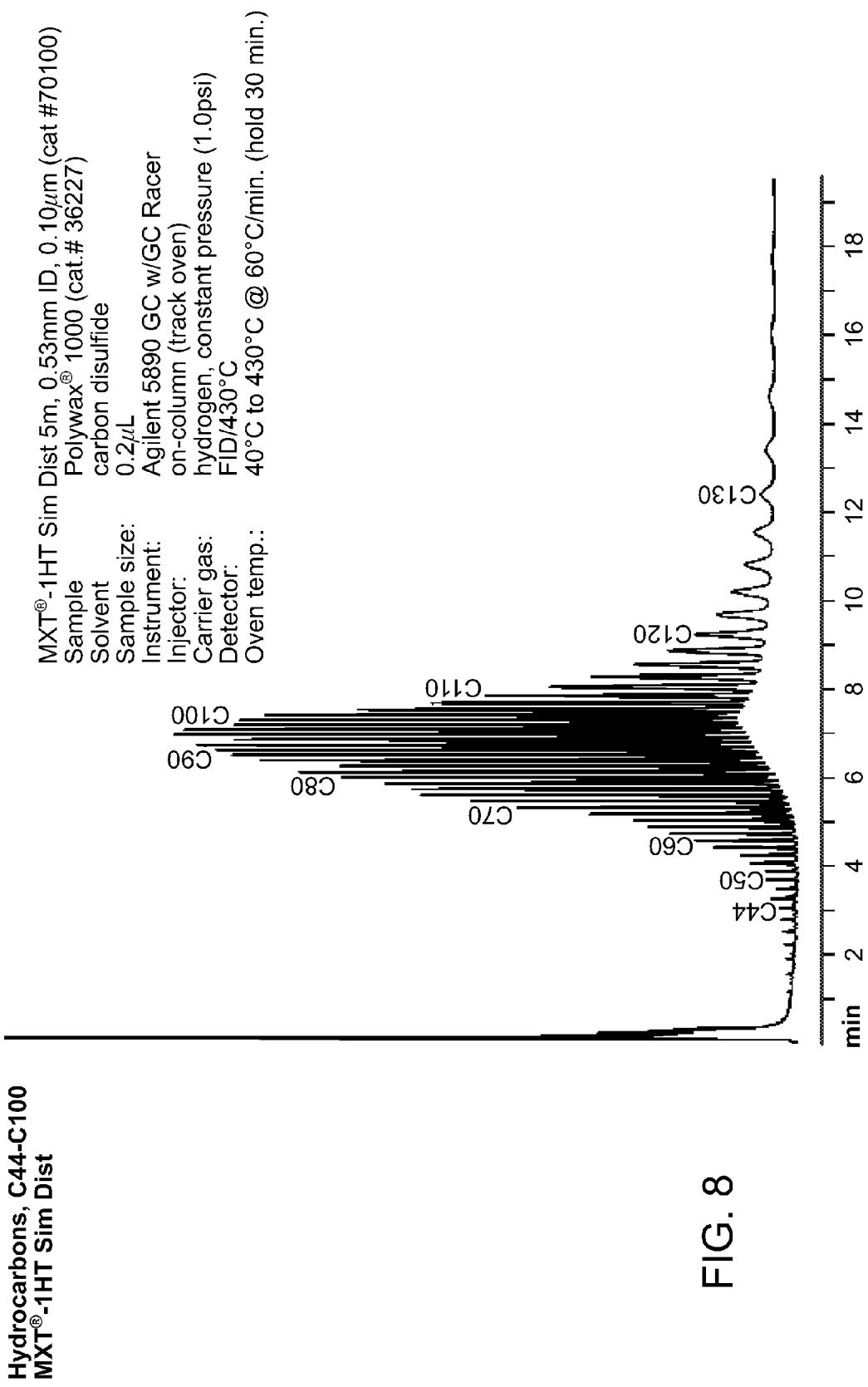
FIG. 8 shows a gas chromatograph of Polywax 1000 (from Restek Corporation).

A Finnigan LTQ mass spectrometer (Thermo Fisher Scientific, San Jose, Calif.) was used for the low resolution experiments and an LTQ Orbitrap from the same company was used for high resolution measurements. Instrumental conditions, unless specified otherwise, were as follows. Inlet capillary temperature: 200° C.; heated-capillary voltage: 15 V; tube-lens voltage: 65V. The experimental setup for ionization from paper was similar to that described in a previous publication (Wang et al., Angew. Chem. Int. Ed. 2010, 49, 877) except that solvent was not used and the paper was placed within the closed, heated chamber of the LTQ normally used for atmospheric pressure chemical ionization experiments. The chamber was filled with nitrogen gas heated to about 350° C. Solvents and other chemicals, including pure alkanes, were purchased from Sigma-Aldrich (St. Louis, Mo.), and were used without further purification. The paper substrate was Grade 1 chromatography paper purchased from Whatman (Maidstone, England). Polywax 1000 was purchased from Restek Corporation (110 Benner Circle, Bellefonte, Pa.). Gas chromatography/flame ionization detection (FID) characterization of Polywax 1000 (data from Restek) is shown in FIG. 8. An unsymmetrical distribution is seen; the most intense signal in the distribution weighted for intensity occurs at ca. $C_{94}$ while the absolute highest intensity occurs at $C_{86}$. The ASTM® D5307 Crude oil qualitative standard was purchased from Sigma-Aldrich. It has 16 alkanes with equal amounts of each component, as shown in Table 3.

TABLE 3

ASTM D5307 Crude oil qualitative standard

|  | molecular weight | M − 1 | M + 14 |
|---|---|---|---|
| Decane | 6.25% | 142 | 141 | 156 |
| Undecane | 6.25% | 156 | 155 | 170 |
| Dodecane | 6.25% | 170 | 169 | 184 |
| Tridecane | 6.25% | 184 | 183 | 198 |
| Tetradecane | 6.25% | 198 | 197 | 212 |
| Pentadecane | 6.25% | 212 | 211 | 226 |
| Hexadecane | 6.25% | 226 | 225 | 240 |
| Heptadecane | 6.25% | 240 | 239 | 254 |
| Octadecane | 6.25% | 254 | 253 | 268 |
| Eicosane | 6.25% | 282 | 281 | 296 |
| Tetracosane | 6.25% | 338 | 337 | 352 |
| Octacosane | 6.25% | 394 | 393 | 408 |
| Dotriacontane | 6.25% | 450 | 449 | 464 |
| Hexatriacontane | 6.25% | 506 | 505 | 520 |
| Tetracontane | 6.25% | 562 | 561 | 576 |
| Tetratetracontane | 6.25% | 618 | 617 | 632 |

Example 2

Alternative System Set-Ups

Figure 14:
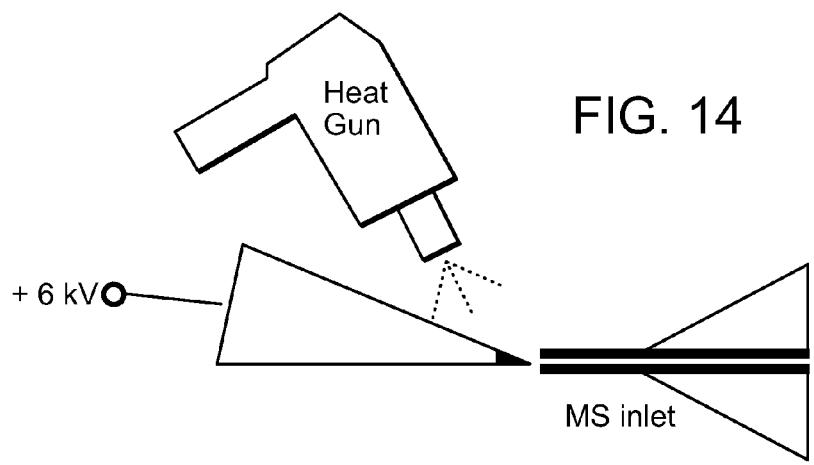
FIG. 14 is a schematic of a system for ambient ionization of alkanes from dry paper.
Figure 15A:
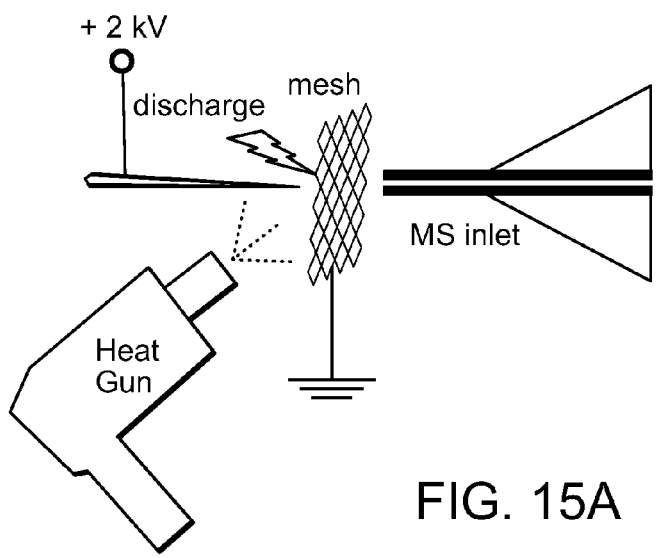
FIG. 15A-B is a schematic of a system for mesh-assisted discharge ionization (may be accompanied by oxidation) of alkanes.
Figure 15B:
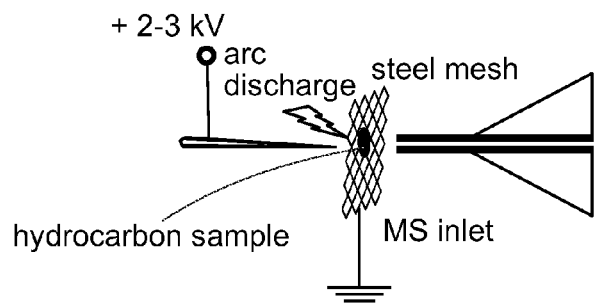

FIGS. 14-15 show alternative system set-ups as to that described above in Example 1 for analysis of alkanes. FIG. 14 shows a system set-up for use in hot open air. The method uses heating at about 300° C. and operates in air. The result is spectra that are dominated by [M−H]$^+$ ions and also include various oxidation products.

FIG. 15 shows a system set-up that involves mesh-assisted arc discharge. This method uses heating and operates in air but the sample is on a stainless steel mesh, not on paper. It was successful for light and medium length alkanes. A system set-up for conducting an arc-discharge technique is described in Li (Analyst, 135, 2010, 688-695).

Figure 9:
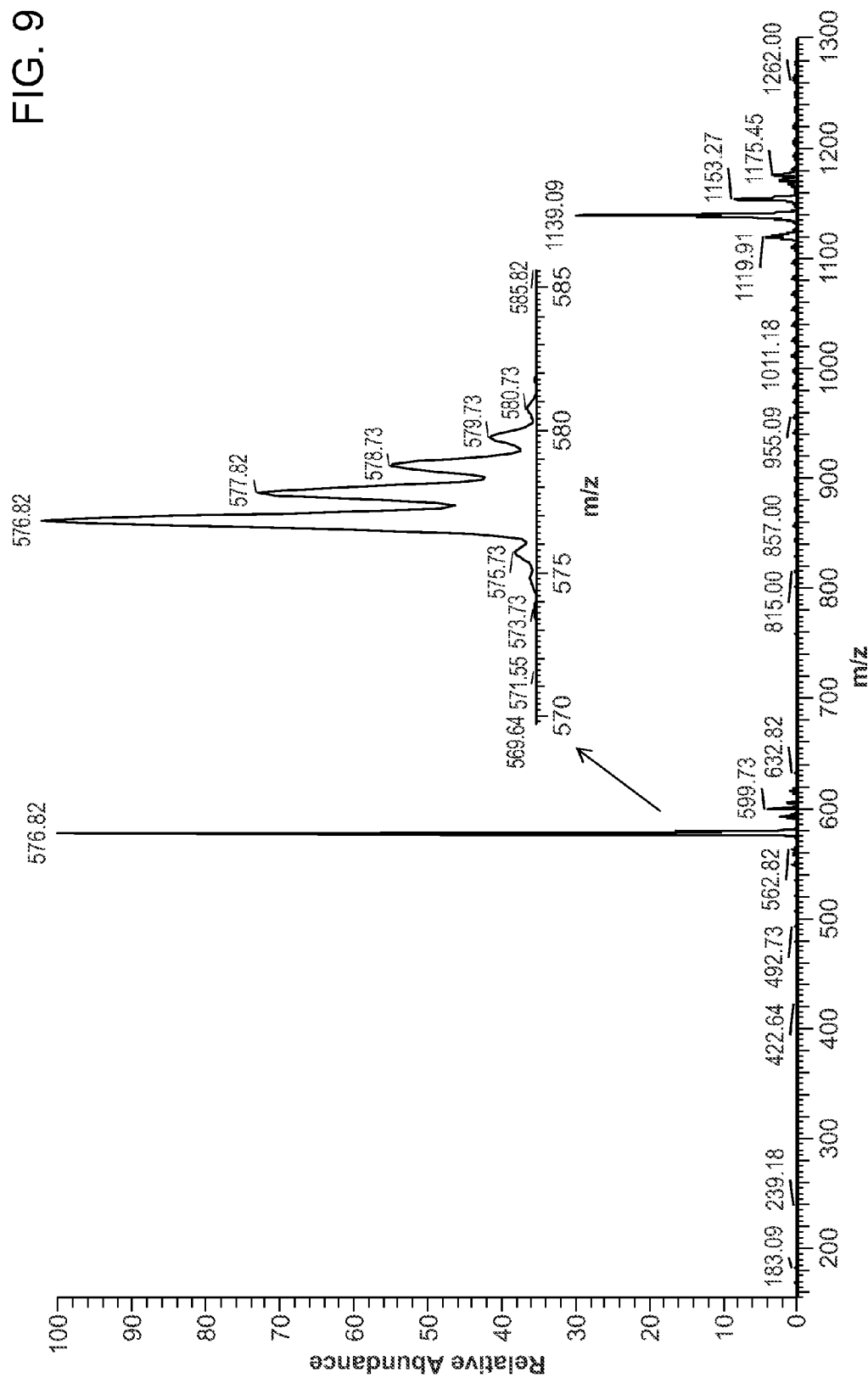
FIG. 9 shows a mass spectrum of $C_{40}H_{82}$ alkane analyzed by methods of the invention. The heated gas was at 250° C.
Figure 10:
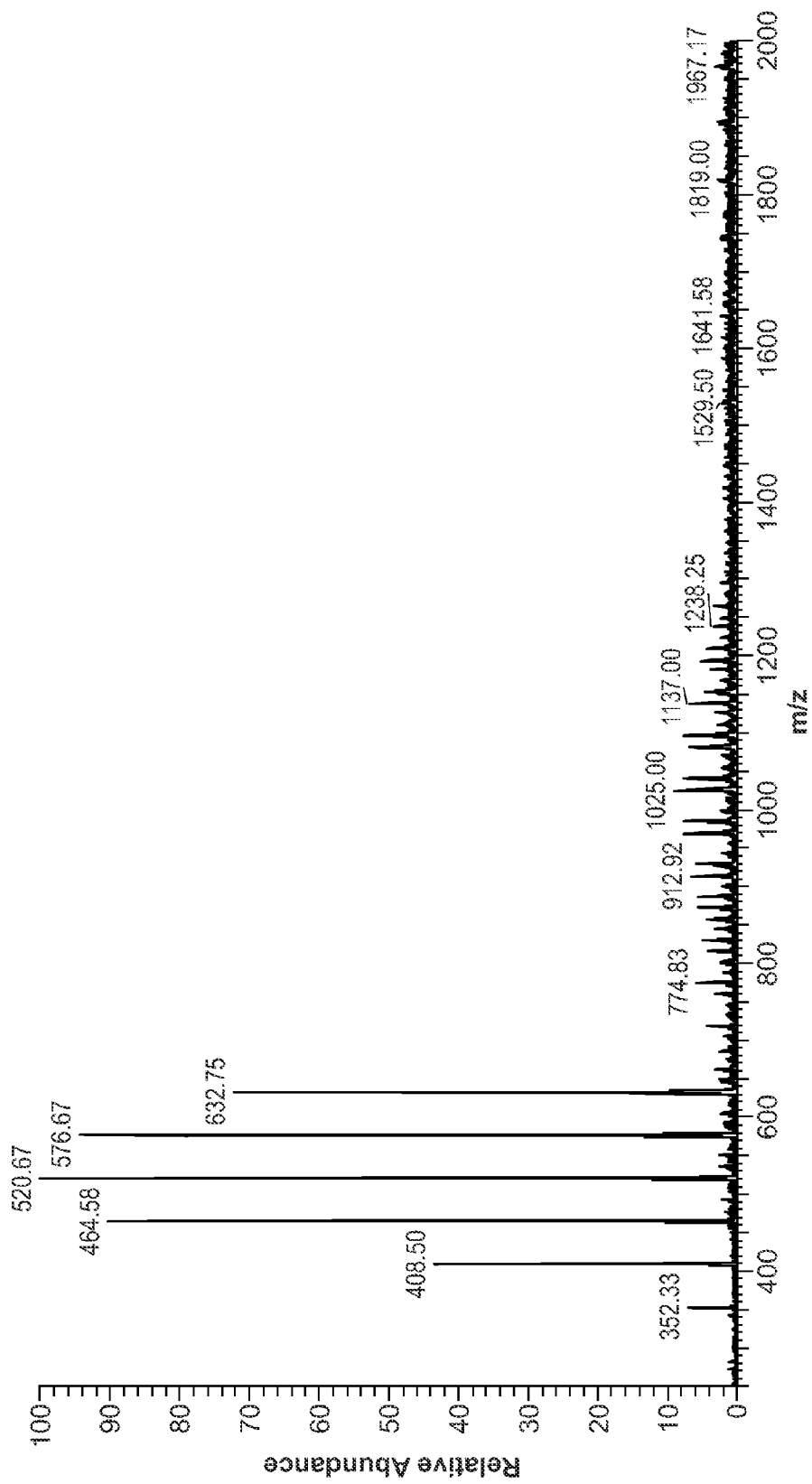
FIG. 10 shows a mass spectrum of oil analyzed by methods of the invention. The heated gas was at 350° C.
Figure 16:
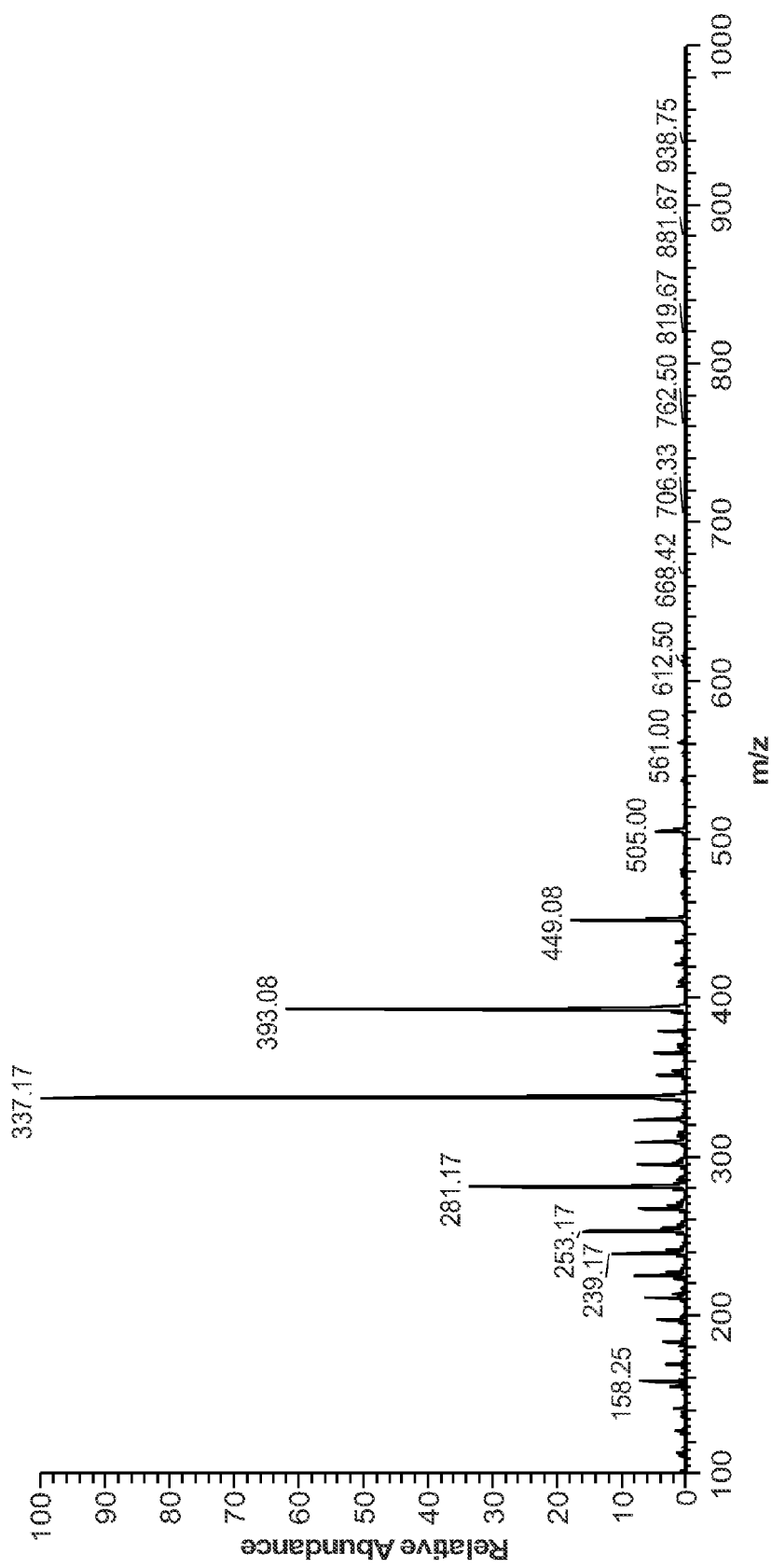
FIG. 16 shows a mass spectrum of oil analyzed by methods of the invention. The heated gas was at 300° C.

Principal features of the data for each of the three experimental methods are: i) Paper spray in a heated chamber, N$_2$ atmosphere, electrically heated to ca. 400° C. for larger n-alkanes (≥C28), gives [M+14]$^+$ viz. [M+N]$^+$ and [M+12]$^+$, viz. [M+N-2H]$^+$, as well as some dimeric ions [2M+N-yH]$^+$ where y=1 and 4 (system set-up described in Example 1). The major reaction formally involves a net N$^+$ transfer to generate the [M+N]$^+$ ions as shown in FIGS. 2, 9, and 10. This represents an unprecedented C—H or C—C substitution, as discussed further below. ii) Paper spray in the open air using a heat gun at a temperature of 300° C., for medium-size alkanes mainly gives [M−H]$^+$; accompanied by various oxygenated species, as shown in FIG. 16. iii) Mesh discharge in open air, using a stainless steel mesh, a heat gun, for light and medium hydrocarbons.

Figure 17:
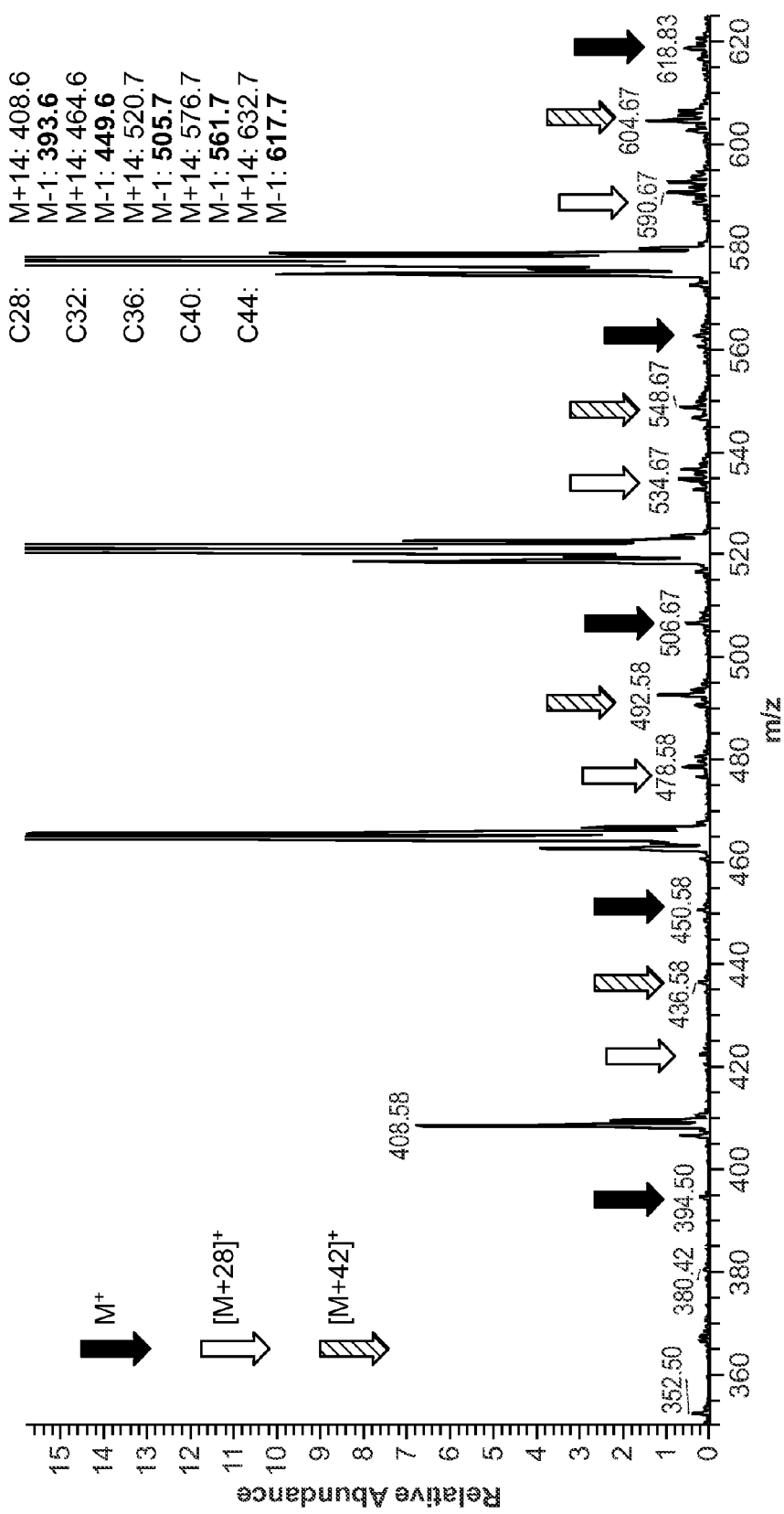
FIG. 17 shows a mass spectrum of an oil.

FIG. 9 shows the formation of the characteristic [M+14]$^+$ and [2M+N-2H]$^+$ ions from a single n-alkane, C$_{40}$H$_{82}$. In addition to the main ions, there are also some minor ions. They include the [M+N+23]$^+$, probably as the result of sodium incorporation. The oil sample (Table 3) gives the expected distribution of lower alkanes (FIG. 10) as well as some small peaks due to dimerization at higher mass when examined by methods conducted with heated nitrogen gas. An expanded view of the crude oil sample (FIG. 17) indicates the presence of a variety of minor ions, amongst which the radical cation, M$^+$. is of most interest.

Figure 18:
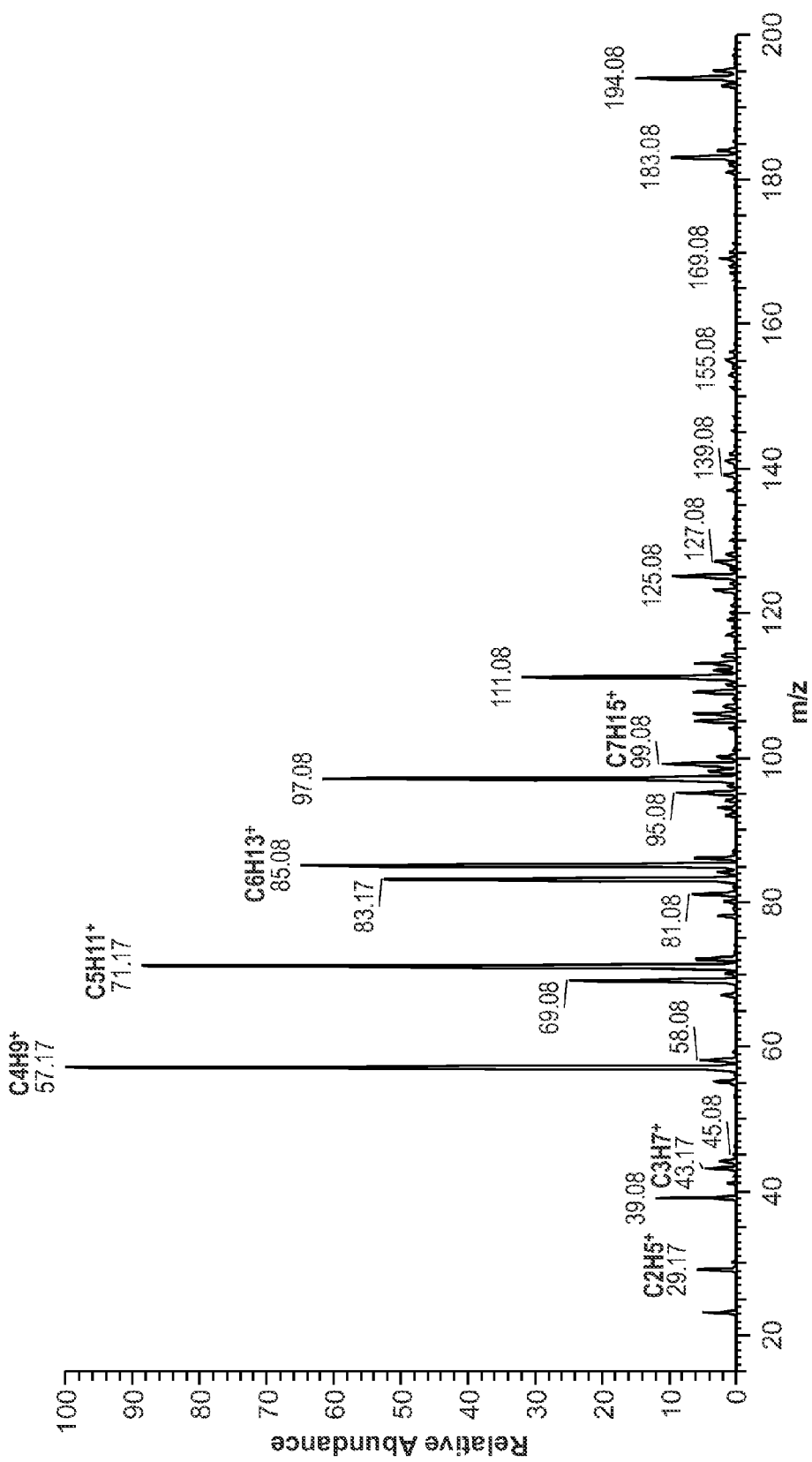
FIG. 18 is a low-mass MS spectrum for Polywax 1000 in $N_2$ atmosphere at 450° C.

Another feature of interest in alkane spectra is the presence at very low mass of alkyl and alkenyl cations, as seen for the Polywax sample in FIG. 18. The abundant C4 to C8 alkyl cations and alkenyl ions could serve as the reagent ions in the atmospheric pressure chemical ionization of the vaporized long-chain alkanes.

The open air heating method was successful for the C$_{3-2}$ alkane, giving prominent [M−H]$^+$ ions at m/z 449, 393, 337 and 281 (FIG. 10). There is data in the literature indicating that [M−H]$^+$ ions can be formed by hydride ion transfer to generate carbocations; this may occur on the surface of field emitters or by field-induced ionic adsorption of unsaturated compounds. The origin of the [M−H]$^+$ ions has also been attributed to field ionization combined with hydrogen transfer from molecules to radical sites of the emitter surface.

The dominant species observed depend on experimental conditions, which can be adjusted to favor [M−H]$^+$ or [M+N]$^+$ as just indicated. If formation of these species is controlled by the size of the alkanes rather than the experimental conditions, then at some alkane size we should see both types of ions in the same spectrum. However, this situation was not encountered. The minor species include M$^+$. (seen for example at C$_{20}$-C$_{44}$, as well as the dimeric ions already mentioned). The [M−H]$^+$ formation process, including experiments with labelled alkanes, suggest that this ion is not generated from the low mass alkyl cations seen in the mass spectra by ion/molecule reactions. The logical alternative to an ion/molecule process for formation of [M−H]$^+$ is a field ionization/desorption process. Following Röllgen, the origin of the [M−H]$^+$ was assigned to field desorption involving proton transfer to the emitter surface. The observation of traces of molecular radical cations (M$^+$.) suggest that a minor component of ionization occurs by simple field ionization. Under these conditions there are also no protonated molecules.

Figure 30:
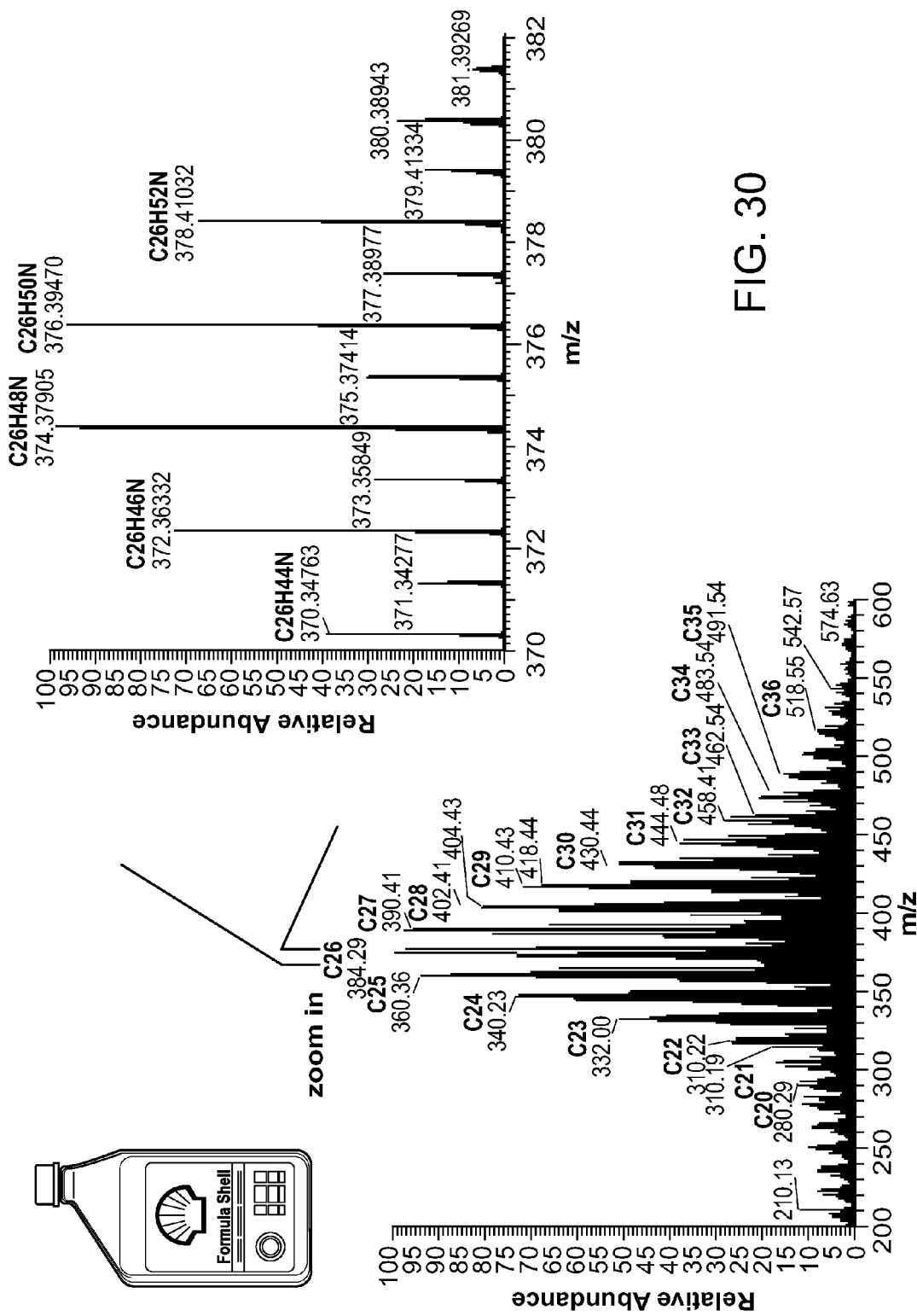
FIG. 30 is an MS spectrum of 10W30 petroleum-based motor oil ionized by arc discharge at 150° C. at $N_2$ atmosphere: all the peaks are mono-nitrogen incorporated.

In the arc-discharge method, instead of applying a potential to the substrate on which the hydrocarbon sample is placed, the sample can be placed on a steel mesh and a corona needle can be used to cause a discharge. Using this arc-discharge method described herein, very similar data are obtained with nitrogen atom incorporation into the alkanes. See FIG. 30.

Figure 19:
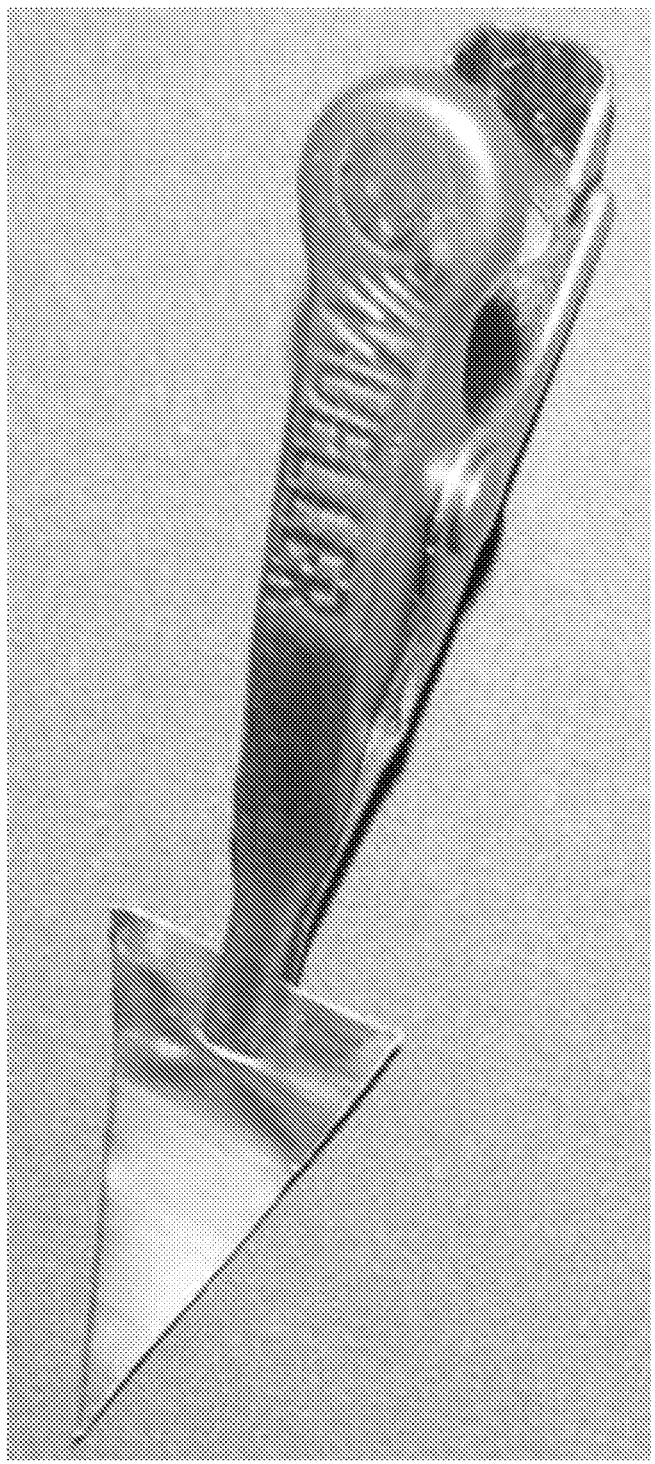
FIG. 19 is a schematic of a system for analysis of alkanes that uses a non-porous substrate.
Figure 20:
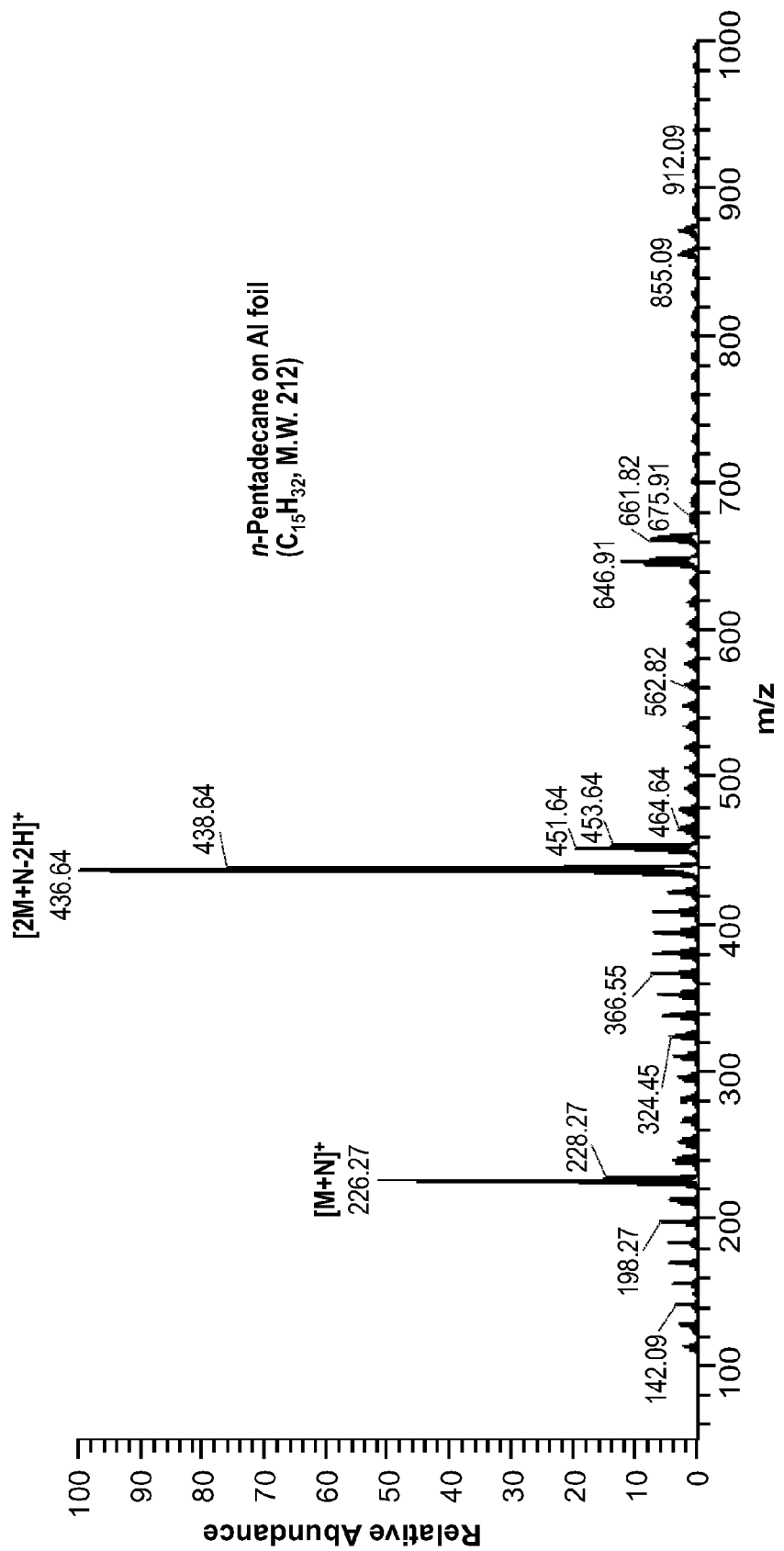
FIG. 20 is an MS spectrum of n-$C_{15}H_{32}$ obtained using the system set-up of FIG. 19.

Another system set-up is shown in FIG. 19. That figure shows a system set-up that uses a non-porous substrate. An exemplary non-porous material is a metal, such as aluminum. The substrate is connected to a high voltage source and the alkane (e.g. wax) is applied to the substrate. The sample is then heated on the substrate to produce ions of the alkane. FIG. 20 shows the mass spectrum of n-C$_{15}$H$_{32}$ recorded from aluminum foil in N$_2$ atmosphere at 200° C., 3 kV, discharge current 4.65 uA, using LTQ and showing [M+N]+ and [2M+N]+, M=C$_{15}$H$_{32}$.

Example 3

Ion Composition and Structure

Figure 21:
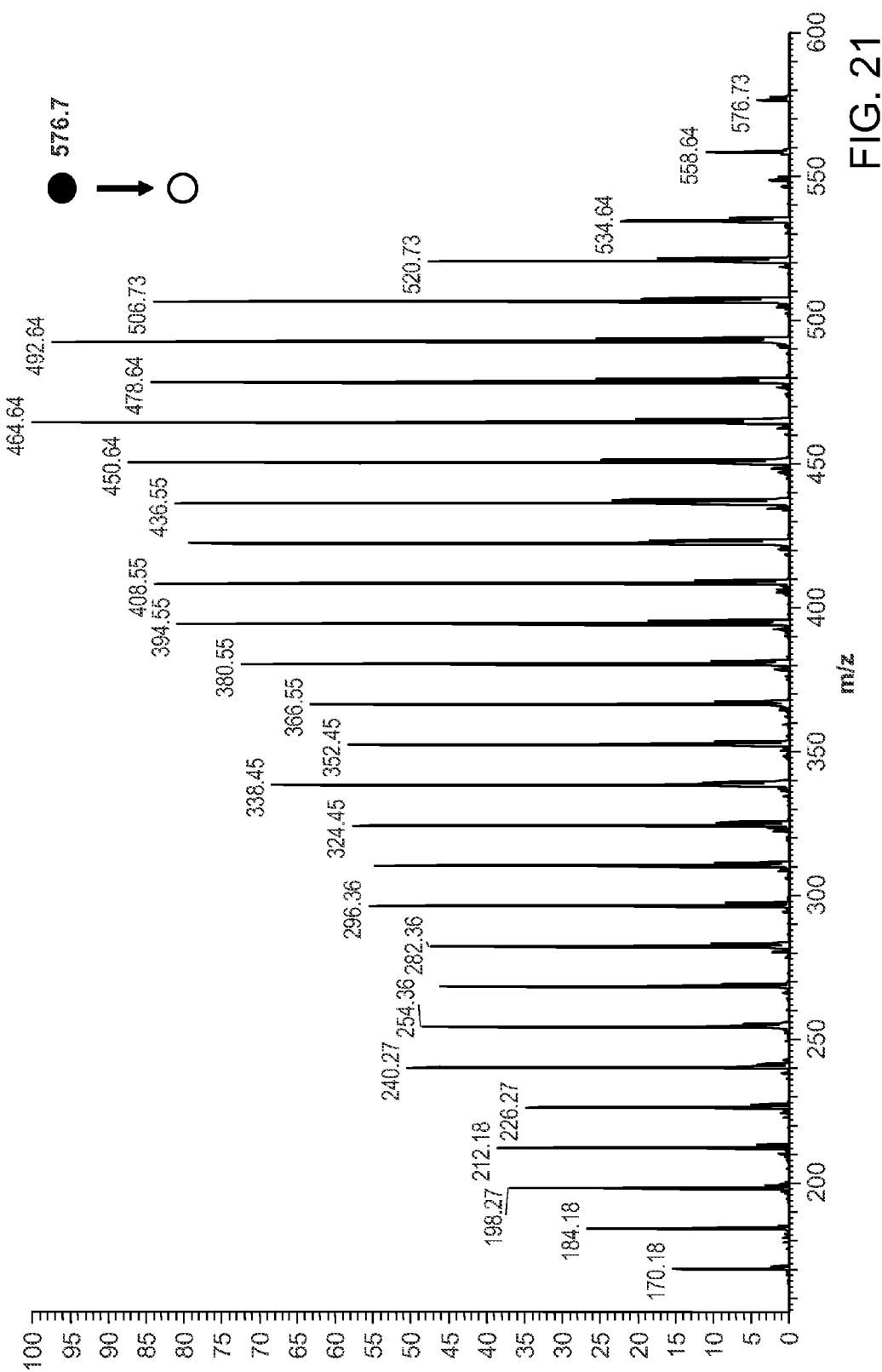
FIG. 21 is an MS/MS spectrum of $[M+N]^+$ ion of $C_{40}H_{82}$ alkane.
Figure 22:
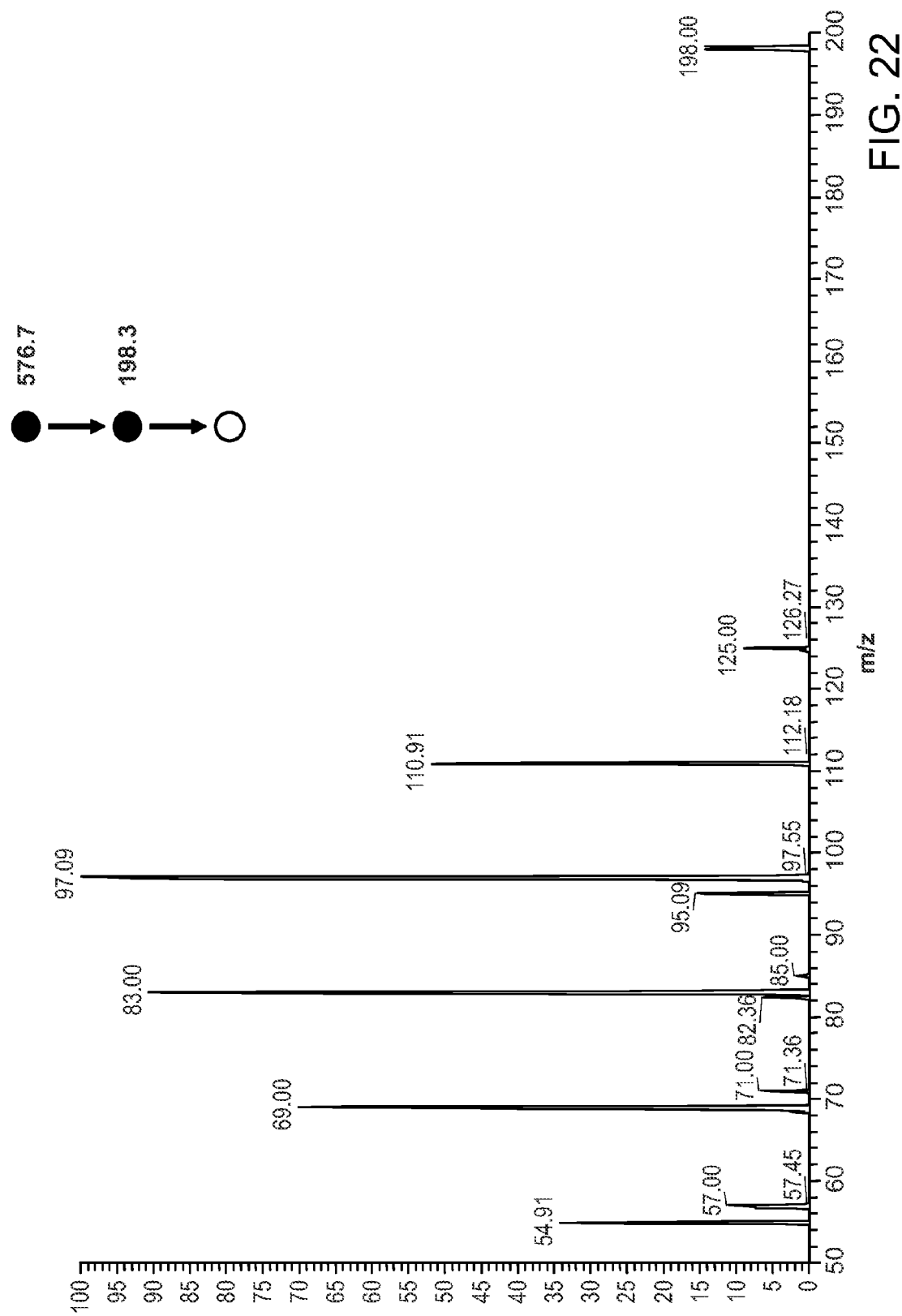
FIG. 22 is an $MS^3$ spectrum of $[M+N]^+$ ion of $C_{40}H_{82}$ alkane.
Figure 23:
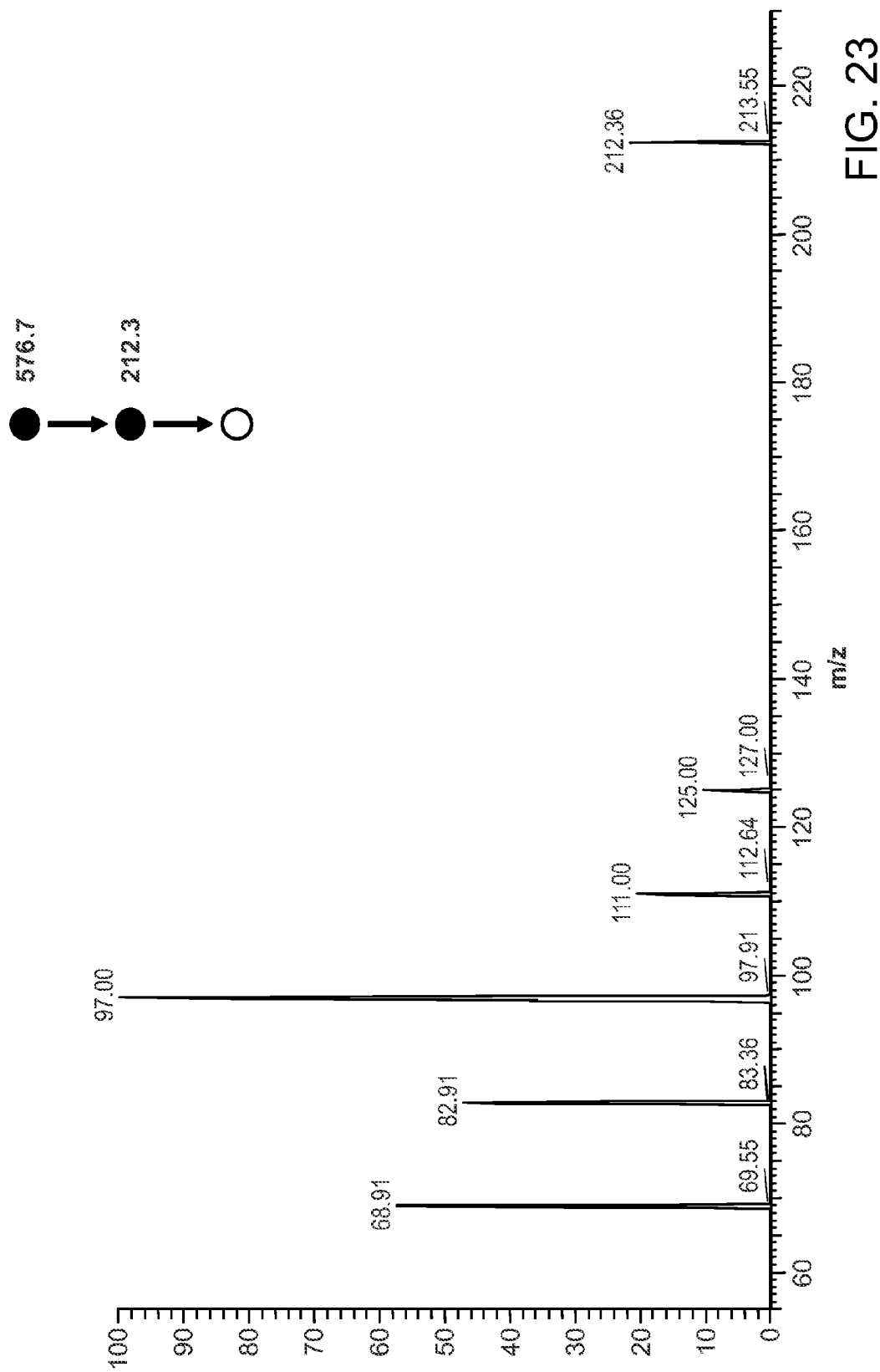
FIG. 23 is an $MS^3$ spectrum of $[M+N]^+$ ion of $C_{40}H_{82}$ alkane.
Figure 24:
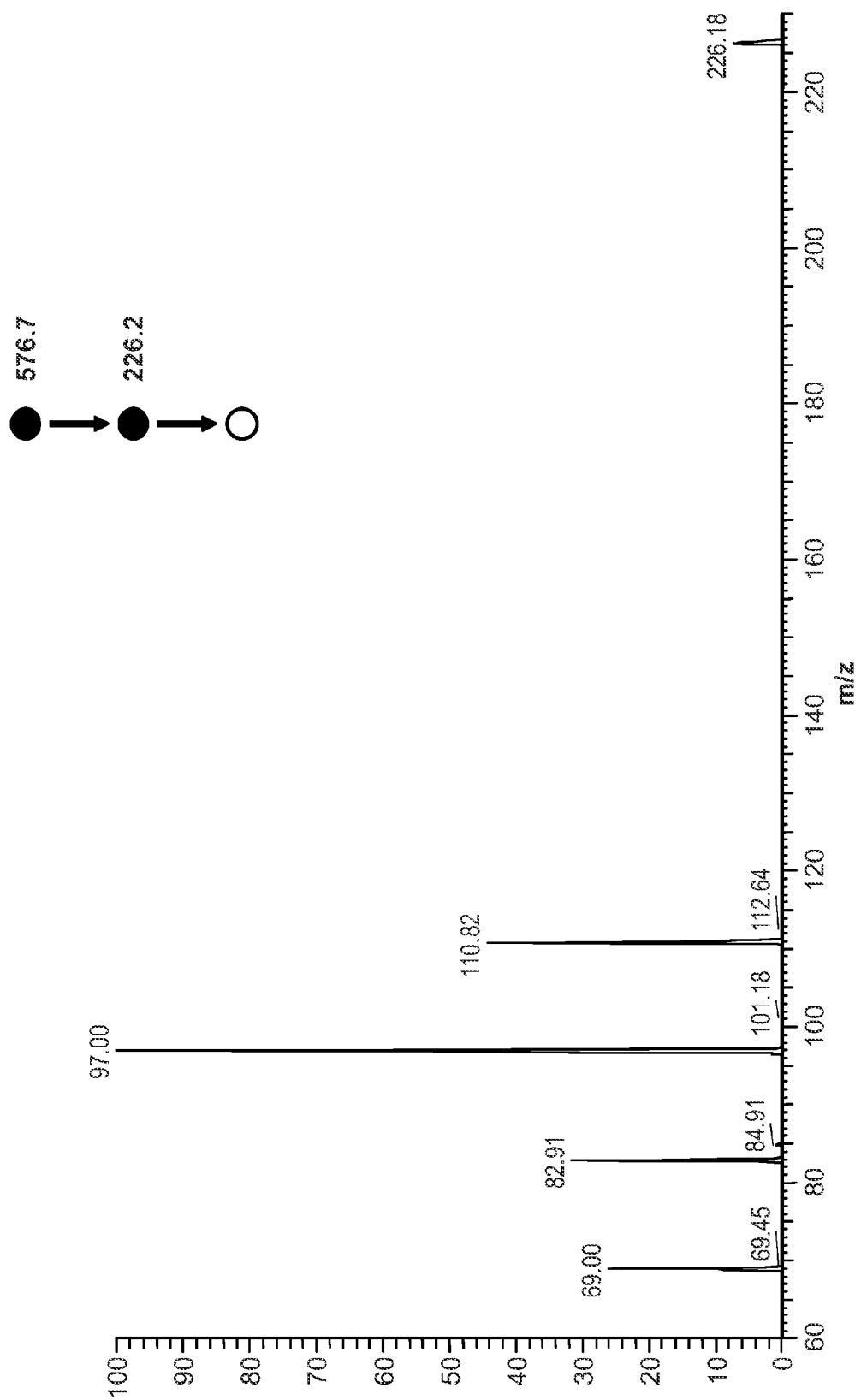
FIG. 24 is an $MS^3$ spectrum of $[M+N]^+$ ion of $C_{40}H_{82}$ alkane.
Figure 25:
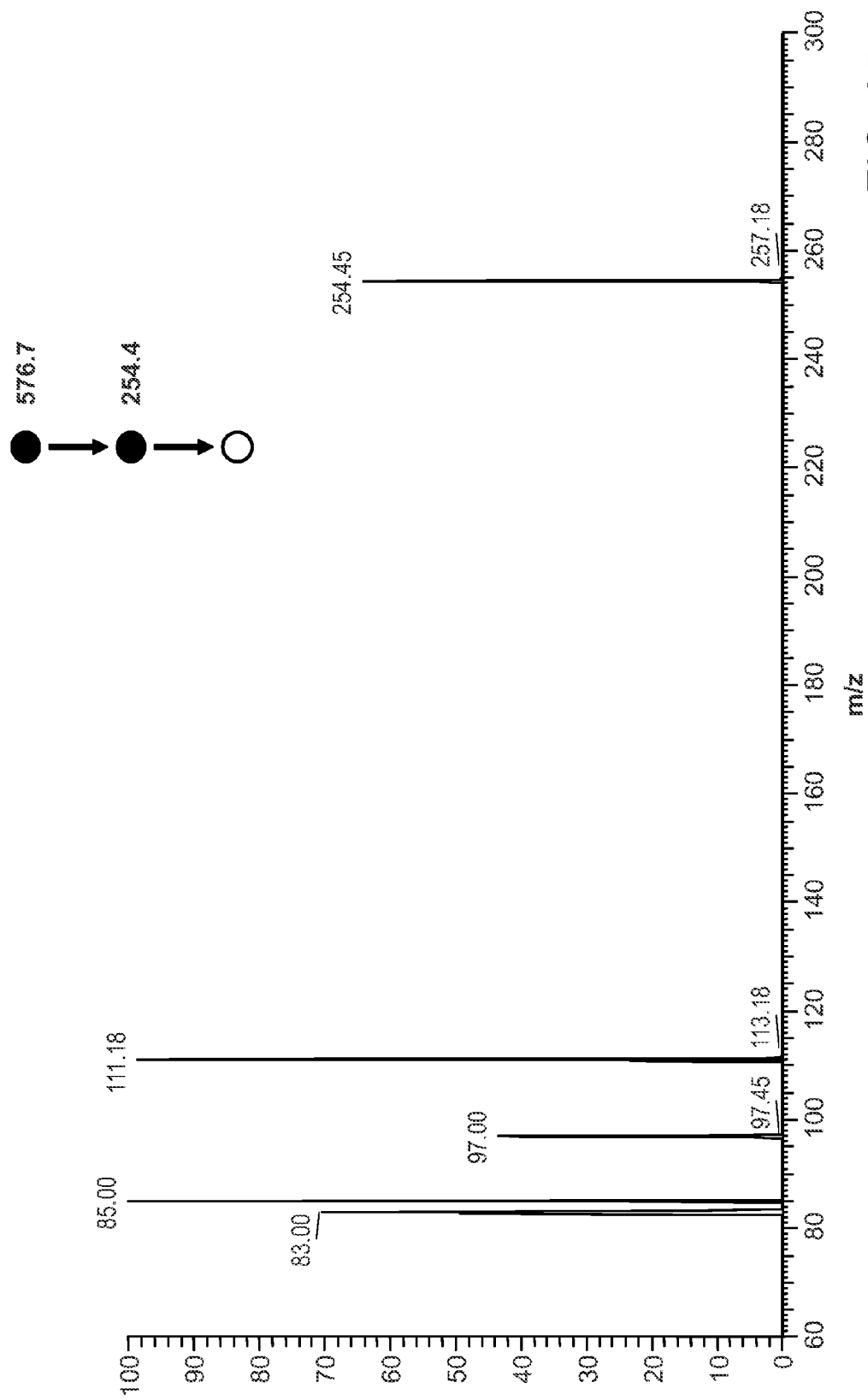
FIG. 25 is an $MS^3$ spectrum of $[M+N]^+$ ion of $C_{40}H_{82}$ alkane.
Figure 26:
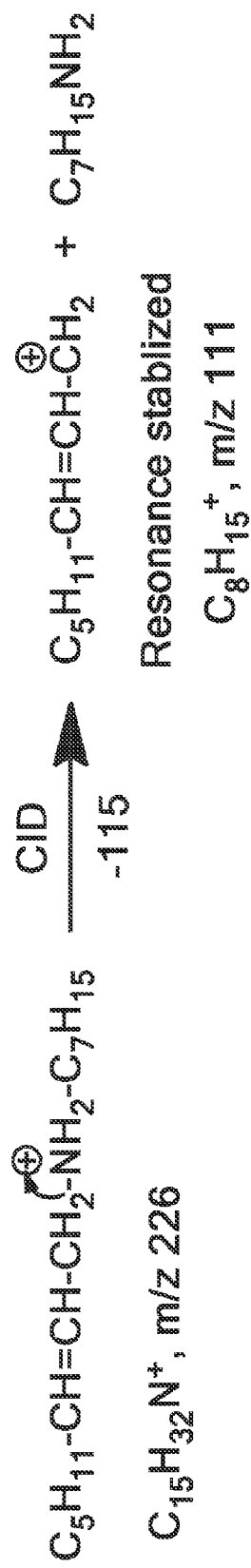
FIG. 26 is a schematic showing a fragmentation mechanism leading to the alkenyl cations seen in the $MS^3$ spectra.

Exact mass measurements were used to confirm the structures of the main ions generated by methods of the invention using heated nitrogen gas. Tandem mass spectrometry and MS$^3$ experiments were used to obtain additional information on these ions. Data are shown in FIGS. 21-25. The MS/MS data is discussed in the detailed description. The lower mass range cannot be observed in the ion trap but the upper region shows products of alkene elimination with peaks at 14 Da intervals (FIG. 21). The lower mass ions are accessible in MS$^3$ experiments and that for representative C$_{40}$H$_{82}$ alkane shows that the intermediate products of alkene elimination, m/z 198, 226, 254, and 296, all behave similarly in (i) not themselves undergoing alkene elimination and (ii) in giving a small set of low mass alkenyl ions (FIGS. 22-25). The first fact indicates the alkene losses observed in the MS/MS spectra are probably largely due to single neutral fragments rather than a series of successive losses. The second fact indicates that the selected intermediate ions fragment with loss of nitrogen and their behavior is best accommodated by assuming that the original $N^+$ insertion occurred near the end of the alkyl chain to create an N,N-alkyl alkenyl amine. Fragmentation of these ions by loss of an alkyl amine gives the alkenyl cation the length of which indicates the position of nitrogen insertion. The data indicate strong preference for $C_6$ to $C_9$ of N insertion. A possible mechanism for the fragmentation in one representative $MS^3$ case (that of m/z 226) is shown in FIG. 26.

Figure 27:
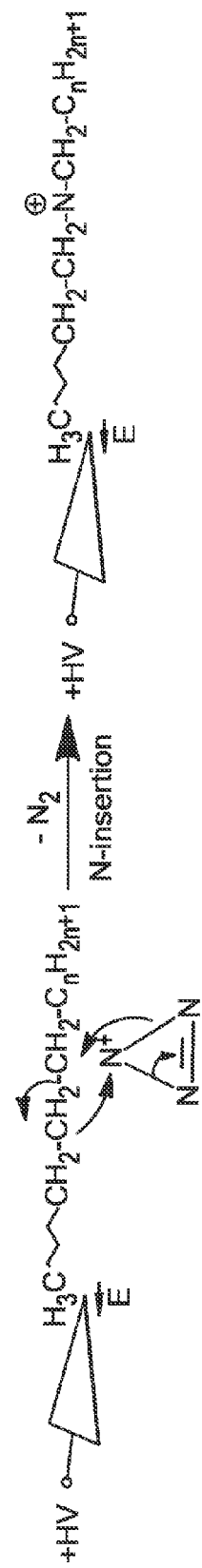
FIG. 27 is a schematic showing a possible mechanism of nitrogen insertion into alkanes on paper substrate. The alkanes are activated by the applied potential.

Thus, the data strongly suggest nitrogen insertion to C—C bonds and that these bonds lie near the ends of the n-alkane chain. This supports the assumption that the bonds are activated by the electric field. It is also in itself evidence that the reactive species responsible to N-insertion is an ion, presumably the azide ion, not the azide radical. This leads one to propose the mechanism of field-assisted alkane activation and azide ion insertion shown in FIG. 27. The alkane molecule is polarized by the charge on the paper leads to induced charges as shown. The favored site of azide cation attack will be at the end of the molecule closest to the paper. Steric factors probably account for the favored reaction some distance in from the chain terminus.

Example 4

Dimeric Ions

Figure 28:
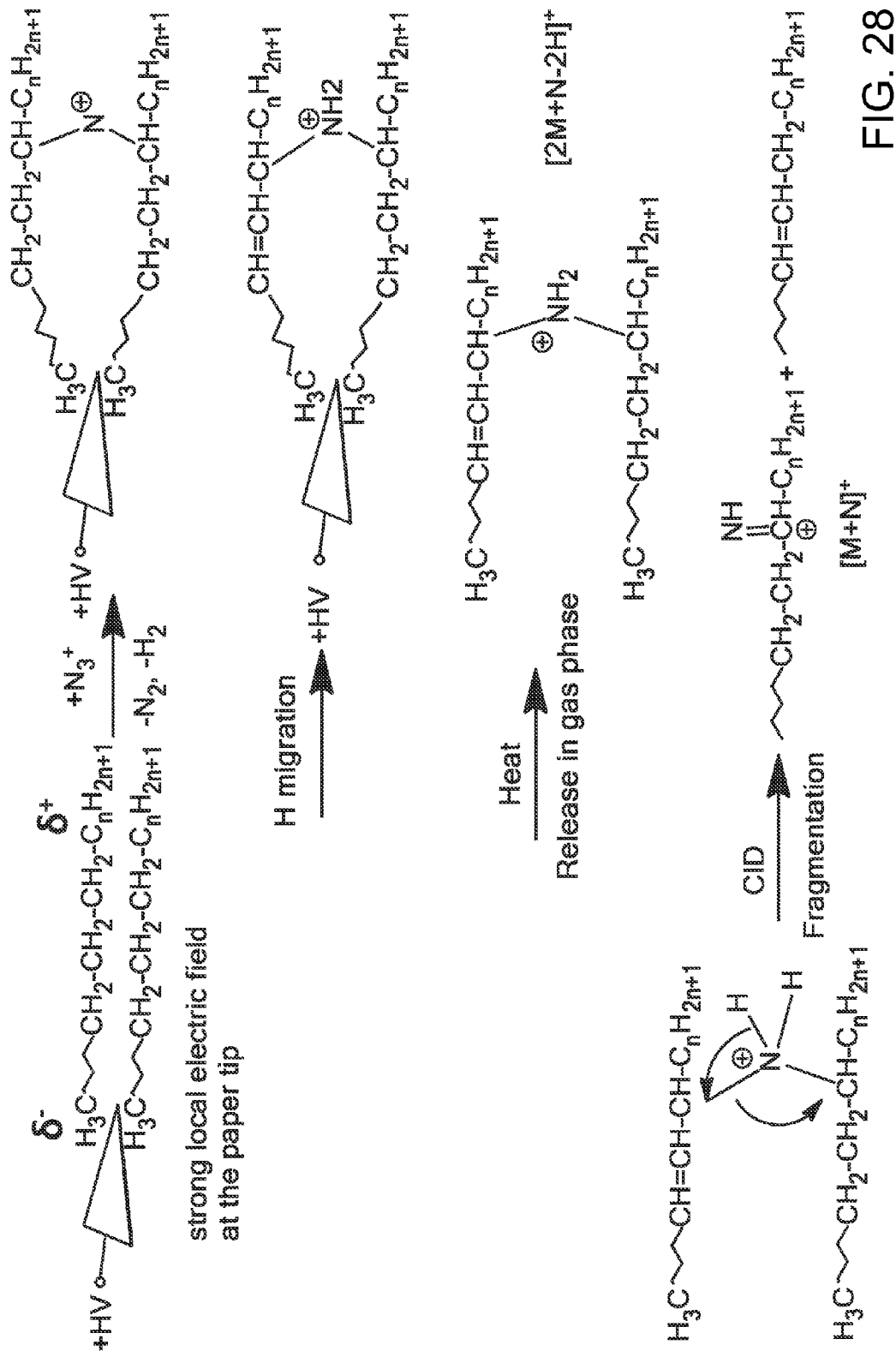
FIG. 28 is a schematic showing a possible mechanism of dimeric ion formation from adjacent alkanes on paper substrate. The alkanes are activated by the applied potential.

The [2M+12] ion is $[2M+N-2H]^+$ based on HRMS measurements. It would involve alkyl transfer with $H_2$ elimination if it occurs from the monomer in an ion/molecule reaction. Hence again, a mechanism involving a field-assisted surface reaction is more feasible, as shown in FIG. 28. The azide ion might generate a new C—C bond between the activated and closely packed chains or the intermediate nitrenium ion generated in an initial intra-chain insertion reaction may react with an adjacent chain to generate the product. In either event, additional energy will be required for desorption of both units which is consistent with increase in dimer relative to monomeric product as the temperature is increased.

There are actually several dimeric ions, $[2M+13]^+$ (ca. 10%), $[2M+12]^+$ (ca. 77%), and $[2M+10]^+$ (ca. 13%). The relative abundances are given after $^{13}C$ correction and are for the $C_{60}H_{122}$ system. Note the formation of the radical cation $[2M+N-H]^+$. The MS/MS data (FIGS. 11-13) of the dimeric ions follow the same pattern as the monomers, showing loss of neutral alkenes, which is consistent with the types of structures proposed. Notable is the fact that the fragmentations are dominated by fragmentation to the monomer, $[M+N]^+$ with the loss of the neutral alkene.

Figure 29:
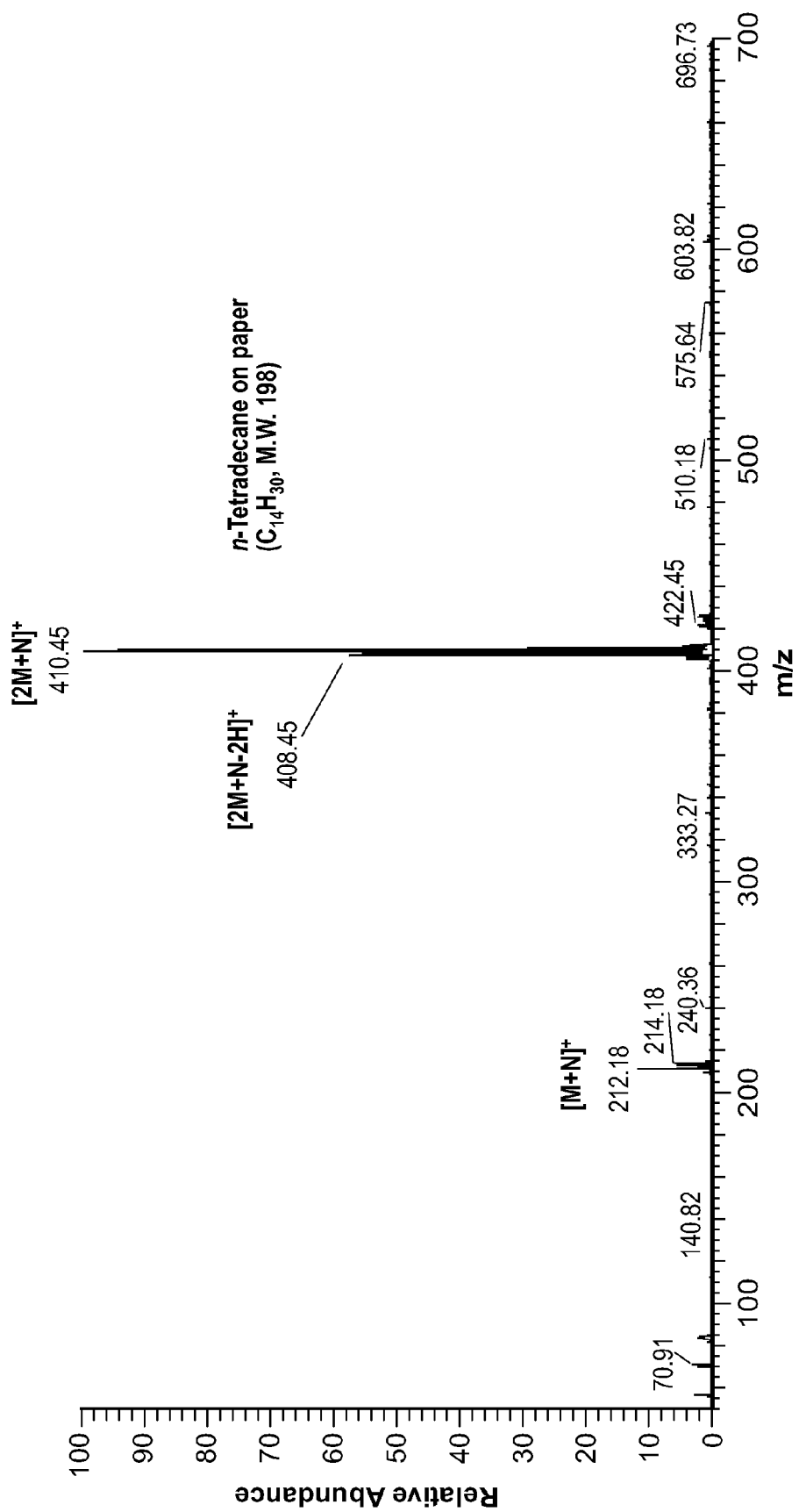
FIG. 29 is an MS spectrum of n-$C_{14}H_{30}$ recorded from filter paper in $N_2$ atmosphere at 50° C., 6 kV, using LTQ and showing $[M+N]^+$ and $[2M+N]^+$, $M=C_{14}H_{30}$.

Additional representative examples of successful N-atom incorporation into smaller alkanes have been recorded. Sometimes in these cases the dimeric ion $[2M+N]^+$ is the base peak. An example is shown in FIG. 29.

Example 5

Nitrogen Atom Sources

The product ion is formally the result of $N^+$ insertion into a C—H or C—C bond of an alkane. The reaction could involve direct $N^+$ insertion from a suitable precursor ion or N-atom insertion followed by ionization. The most abundant reagent ion in atmospheric pressure $N_2$ discharges is $N_4^+$. with the trimer $N_3^+$ also prominent. Likely causes for the direct reaction therefore are transfer of $N^+$ and elimination of $N_2$ or $N_3$. The N-atom insertion route would likely involve the azide radical as precursor.

The $N_3$ radical has almost the same heat of formation as $N_2(1\Sigma_g^+)+N(^4S)$—just 0.05+/−0.10 eV higher—although it is kinetically stable. The $N_3^+$ cation is known from its occurrence in $N_2$ discharges but there is no experimental ion/molecule chemistry and no thermochemistry in the literature. There is not thermochemical data on the $N_4^+$. radical cation, the other possible but less likely reagent ion.

Example 6

Chemical Modification and Collection of Waxes

The activation and functionalization of aliphatic C—H bonds has been studied intensively over the past few decades, mainly through reactions involved with transition-metal species (Lech et al., *J. Am. Chem. Soc.* 111, 8588 (1989); Schwarz, *Pure Appl. Chem.* 72, 2319 (2000); and Labinger, *Nature* 417, 507 (2002). Here, we report a different strategy to achieve selective C—H bond activation of saturated alkanes to generate nitrogen inserted ionic species with the nitrogen source being chemically inert dinitrogen. The functionalized species was collected directly at atmospheric pressure as it emerged from the ion source without involving mass analysis.

Optimized conditions for alkane ionization from dry paper in a nitrogen atmosphere were used to produce the data shown. The experiment was done in a $N_2$ atmosphere in an isolated chamber normally used for atmospheric pressure chemical ionization, electrically heated to 200° C., with a potential of 5-6 kV applied to the paper holding the sample. Nitrogen gas has a minimum purity of 99.9% and it was passed at a rate of 5-15 L/min during operation. Ion collection at atmospheric pressure was performed by directing the paper substrate containing the hydrocarbon and floated at +5 kV was directed toward a grounded Au/Si wafer substrate (10 mm away), in a heated nitrogen stream was introduced with gas flow rate of 10 L/min to maintain the nitrogen atmosphere. The Au/Si wafer was cooled using liquid nitrogen to retain the deposited species. After one hour of ion collection, the wafer was allowed to warm to room temperature for FT-IR measurement. The wafer was also rinsed using hexane and the rinsed effluent was analyzed by nanoESI.

Figure 31A:
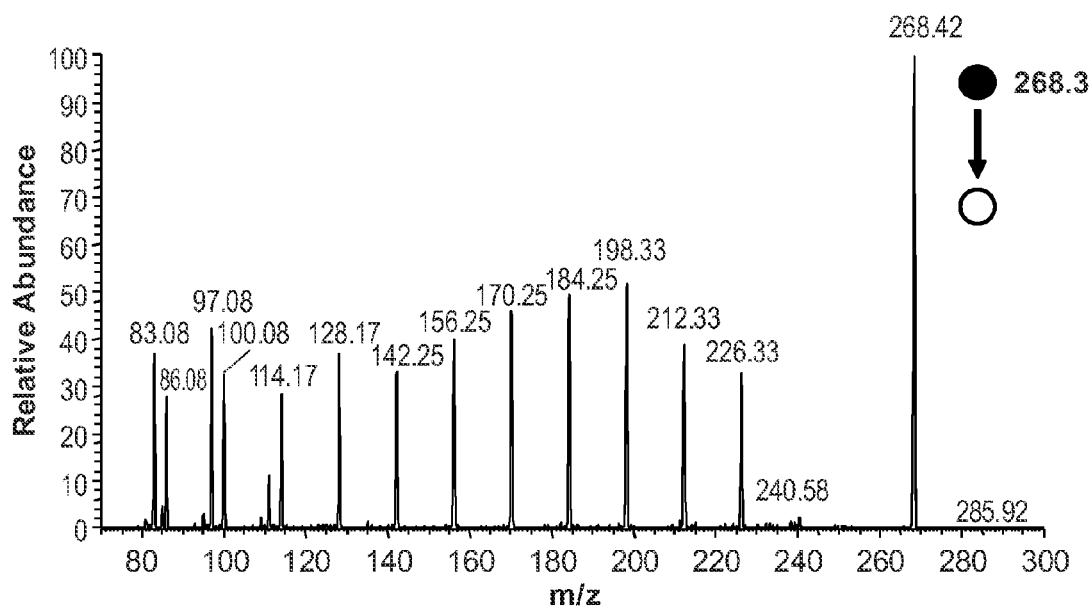
FIGS. 31A and 31B are MS/MS spectra of (FIG. 31A) $[M+N]^+$ ion of n-$C_{18}H_{38}$ alkane recorded on line (FIG. 31B) m/z 268.3 peak from nanoESI analysis of rinsed sample after deposition of $[M+H]^+$ and other ions at atmospheric pressure during reactive ionization of n-$C_{18}H_{38}$.
Figure 31B:
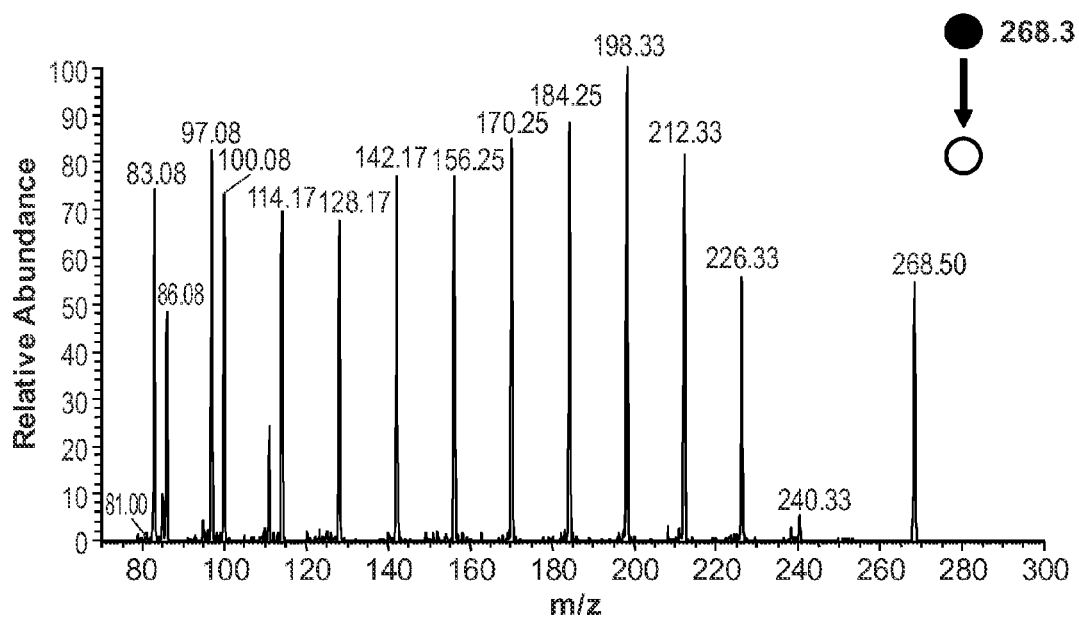

First, the n-$C_{18}H_{38}$alkane was deposited in microgram amounts as a thin film onto the tip of a filter paper triangle, and a potential of 5-6 kV was applied in a heated nitrogen atmosphere (ca. 200° C.). The resulting mass spectrum was dominated by just two ions: $[M+N]^+$ and $[2M+N-2H]^+$, where M represents the examined alkane, which is verified by exact mass measurements. The $[M+N]^+$ signal lasted a long period of time (typically >1 h) with no appreciable diminution during ionization of the wax. The resulting ions was deposited on an inert surface and collected. They were deposited onto an Au substrate at atmospheric pressure without the ions entering the mass spectrometer. The nanoESI MS/MS spectra of the collected sample was identical in all respects to that of the $[M+N]^+$ ion generated on line and recorded during the ionization event (FIG. 31). This confirms successful deposition of the nitrogen-inserted alkane species.

Figure 32:
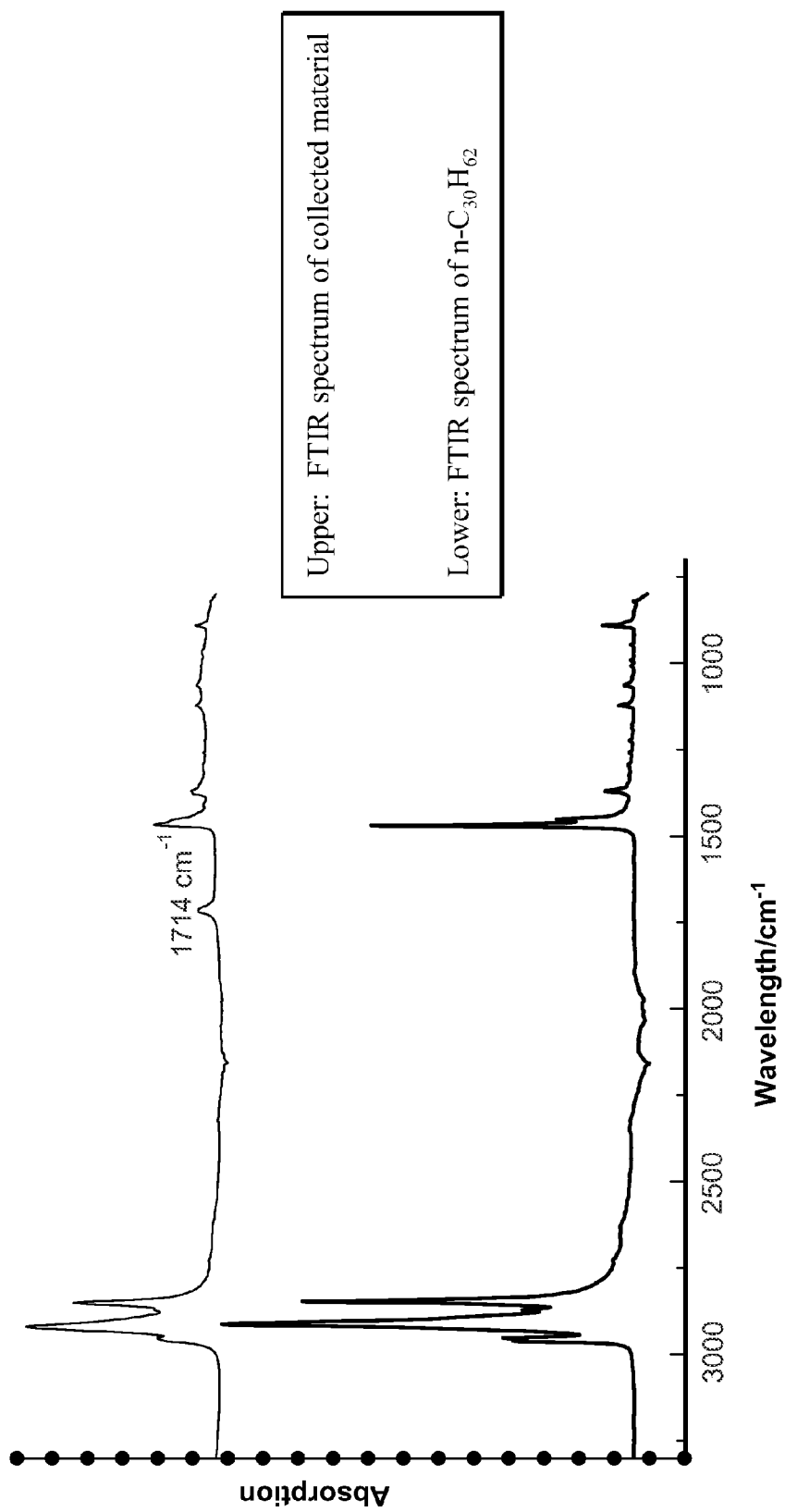
FIG. 32 is an FT-IR spectrum of triacontane (n-$C_{30}H_{62}$) and of other material deposited when collecting $[M+N]^+$ and other ions of triacontane ionized by paper spray in a nitrogen atmosphere. Note the new peak at 1714 $cm^{-1}$ corresponding to an unsaturated alkylamine.

The FT-IR spectrum of the collected sample showed one new absorption peak near 1714 $cm^{-1}$ (FIG. 32), assigned as the C=N stretching of a ketamine or aldimine based on the frequency predicted from ab initio RHF calculations. The lack of ammonia elimination in the MS/MS spectra of $[M+N]^+$ of linear alkanes strongly suggests that nitrogen was inserted into a C—C rather than a C—H bond. The interpretation is consistent with data for N-insertion into cycloalkanes, where ammonia loss is abundant when nitrogen is inserted into non-terminal C—H bonds. MS/MS of [M+N]$^+$ showed that the smallest fragment ion detected by Orbitrap had m/z of 58.0656(7), which has the formula of $C_3H_8N^+$, also suggesting nitrogen locates near the end of the aliphatic chain. Based on the above analysis, nitrogen is likely not very selectively inserted into near-terminal C—C bonds of linear alkanes.

What is claimed is:

1. A system for analyzing a sample, the system comprising:
a probe comprising a substrate that tapers to a tip, wherein the substrate is configured to hold a sample and the substrate is connected to a high voltage source for generating a voltage;
a heating device for generating a heated gas; and
a mass spectrometer that comprises a mass analyzer, wherein the system is configured such that the voltage generated from the high voltage source and the heated gas generated from the heating device are simultaneously applied to the substrate in order to desorb and ionize a sample from the substrate and an inlet of the mass spectrometer is operably associated with the substrate to receive ions of the sample.

2. The system according to claim 1, wherein the heated gas is directed at the probe.

3. The system according to claim 1, wherein the heated gas is directed at the tip of the probe.

4. The system according to claim 1, further comprising a chamber configured to encompass the probe and the device for generating the heated gas.

5. The system according to claim 1, wherein the gas is nitrogen.

6. The system according to claim 1, wherein the probe is composed of a porous material.

7. The system according to claim 1, wherein the probe is composed of a non-porous material.

8. The system according to claim 7, wherein the non-porous material is a metal.

9. The system according to claim 1, wherein the mass analyzer is for a mass spectrometer or a handheld mass spectrometer.

10. The system according to claim 9, wherein the mass analyzer is selected from the group consisting of: a quadrupole ion trap, a rectalinear ion trap, a cylindrical ion trap, a ion cyclotron resonance trap, and an orbitrap.

11. A method for analyzing a sample, the method comprising:
contacting a sample to a substrate that tapers to a tip;
simultaneously applying high voltage and heat to the substrate to generate ions of an analyte in the sample that are expelled from the substrate; and
analyzing the expelled ions.

12. The method according to claim 11, wherein the heat is produced from a heated gas.

13. The method according to claim 12, wherein the heated gas is directed at the substrate.

14. The method according to claim 13, wherein the heated gas is directed at the tip of the substrate.

15. The method according to claim 12, wherein the gas is nitrogen.

16. The method according to claim 11, wherein the substrate is composed of a porous material.

17. The method according to claim 11, wherein the substrate is composed of a non-porous material.

18. The method according to claim 11, wherein the applying step is conducted within an enclosed chamber.

19. The method according to claim 11, wherein analyzing comprises providing a mass analyzer to generate a mass spectrum of analytes in the sample.

20. The method according to claim 11, wherein the method is performed under ambient conditions.

21. A method for ionizing a sample, the method comprising:
simultaneously applying high voltage and heat to a a sample disposed on a substrate that tapers to a tip to generate ions of an analyte in the sample.

* * * * *